US011660022B2

(12) United States Patent
Assouline et al.

(10) Patent No.: US 11,660,022 B2
(45) Date of Patent: May 30, 2023

(54) ADAPTIVE SKELETAL JOINT SMOOTHING

(71) Applicant: Snap Inc., Santa Monica, CA (US)

(72) Inventors: Avihay Assouline, Tel Aviv (IL);
Itamar Berger, Hod Hasharon (IL);
Gal Dudovitch, Tel Aviv (IL); Matan Zohar, Rishon LeZion (IL)

(73) Assignee: Snap Inc., Santa Monica, CA (US)

( * ) Notice: Subject to any disclaimer, the term of this patent is extended or adjusted under 35 U.S.C. 154(b) by 390 days.

(21) Appl. No.: 16/949,607

(22) Filed: Nov. 6, 2020

(65) Prior Publication Data
US 2022/0125337 A1    Apr. 28, 2022

Related U.S. Application Data

(60) Provisional application No. 63/198,553, filed on Oct. 27, 2020.

(51) Int. Cl.
| | | |
|---|---|---|
| *A61B 5/11* | (2006.01) | |
| *G06T 19/00* | (2011.01) | |
| *A61B 5/00* | (2006.01) | |
| *G06T 5/00* | (2006.01) | |

(52) U.S. Cl.
CPC .......... *A61B 5/1113* (2013.01); *A61B 5/744* (2013.01); *G06T 5/002* (2013.01); *G06T 19/006* (2013.01); *G06T 2207/20182* (2013.01); *G06T 2210/41* (2013.01)

(58) Field of Classification Search
CPC ....... A61B 5/1113; A61B 5/744; G06T 5/002; G06T 19/006; G06T 2207/20182; G06T 2210/41

USPC ........................................................ 702/191
See application file for complete search history.

(56) References Cited

U.S. PATENT DOCUMENTS

| | | | |
|---|---|---|---|
| 5,880,731 A | 3/1999 | Liles et al. | |
| 6,020,891 A | 2/2000 | Rekimoto | |
| 6,023,270 A | 2/2000 | Brush, II et al. | |
| 6,038,295 A | 3/2000 | Mattes | |

(Continued)

FOREIGN PATENT DOCUMENTS

| | | |
|---|---|---|
| CA | 2887596 A1 | 7/2015 |
| CN | 109863532 A | 6/2019 |

(Continued)

OTHER PUBLICATIONS

"U.S. Appl. No. 16/951,939, Response filed Nov. 17, 2022 to Non Final Office Action dated Aug. 18, 2022", 9 pgs.

(Continued)

*Primary Examiner* — Aditya S Bhat
(74) *Attorney, Agent, or Firm* — Schwegman Lundberg & Woessner, P.A.

(57) ABSTRACT

Aspects of the present disclosure involve a system comprising a computer-readable storage medium storing a program and a method for performing operations comprising: receiving a video that includes a depiction of a body of a user; detecting a plurality of skeletal joints of the body depicted in the video; tracking movement of the plurality of skeletal joints across a set of frames of the video; and smoothing the movement of a first set of the plurality of skeletal joints between frames in the first set of frames independently of smoothing movement of a second set of the plurality of skeletal joints in the first set of frames.

20 Claims, 11 Drawing Sheets

(56) References Cited

U.S. PATENT DOCUMENTS

| | | |
|---|---|---|
| 6,223,165 B1 | 4/2001 | Lauffer |
| 6,772,195 B1 | 8/2004 | Hatlelid et al. |
| 6,842,779 B1 | 1/2005 | Nishizawa |
| 6,980,909 B2 | 12/2005 | Root et al. |
| 7,173,651 B1 | 2/2007 | Knowles |
| 7,342,587 B2 | 3/2008 | Danzig et al. |
| 7,411,493 B2 | 8/2008 | Smith |
| 7,468,729 B1 | 12/2008 | Levinson |
| 7,535,890 B2 | 5/2009 | Rojas |
| 7,636,755 B2 | 12/2009 | Blattner et al. |
| 7,639,251 B2 | 12/2009 | Gu et al. |
| 7,775,885 B2 | 8/2010 | Van Luchene et al. |
| 7,859,551 B2 | 12/2010 | Bulman et al. |
| 7,885,931 B2 | 2/2011 | Seo et al. |
| 7,925,703 B2 | 4/2011 | Dinan et al. |
| 8,088,044 B2 | 1/2012 | Tchao et al. |
| 8,095,878 B2 | 1/2012 | Bates et al. |
| 8,108,774 B2 | 1/2012 | Finn et al. |
| 8,117,281 B2 | 2/2012 | Robinson et al. |
| 8,130,219 B2 | 3/2012 | Fleury et al. |
| 8,131,597 B2 | 3/2012 | Hudetz |
| 8,146,005 B2 | 3/2012 | Jones et al. |
| 8,151,191 B2 | 4/2012 | Nicol |
| 8,199,747 B2 | 6/2012 | Rojas et al. |
| 8,253,746 B2 | 8/2012 | Geisner et al. |
| 8,332,475 B2 | 12/2012 | Rosen et al. |
| 8,384,719 B2 | 2/2013 | Reville et al. |
| RE44,054 E | 3/2013 | Kim |
| 8,396,708 B2 | 3/2013 | Park et al. |
| 8,425,322 B2 | 4/2013 | Gillo et al. |
| 8,458,601 B2 | 6/2013 | Castelli et al. |
| 8,462,198 B2 | 6/2013 | Lin et al. |
| 8,484,158 B2 | 7/2013 | Deluca et al. |
| 8,495,503 B2 | 7/2013 | Brown et al. |
| 8,495,505 B2 | 7/2013 | Smith et al. |
| 8,504,926 B2 | 8/2013 | Wolf |
| 8,559,980 B2 | 10/2013 | Pujol |
| 8,564,621 B2 | 10/2013 | Branson et al. |
| 8,564,710 B2 | 10/2013 | Nonaka et al. |
| 8,581,911 B2 | 11/2013 | Becker et al. |
| 8,597,121 B2 | 12/2013 | del Valle |
| 8,601,051 B2 | 12/2013 | Wang |
| 8,601,379 B2 | 12/2013 | Marks et al. |
| 8,632,408 B2 | 1/2014 | Gillo et al. |
| 8,633,913 B1 | 1/2014 | Raghu et al. |
| 8,648,865 B2 | 2/2014 | Dawson et al. |
| 8,659,548 B2 | 2/2014 | Hildreth |
| 8,683,354 B2 | 3/2014 | Khandelwal et al. |
| 8,692,830 B2 | 4/2014 | Nelson et al. |
| 8,718,333 B2 | 5/2014 | Wolf et al. |
| 8,724,622 B2 | 5/2014 | Rojas |
| 8,730,156 B2 | 5/2014 | Weising et al. |
| 8,749,557 B2 | 6/2014 | Evertt et al. |
| 8,810,513 B2 | 8/2014 | Ptucha et al. |
| 8,812,171 B2 | 8/2014 | Filev et al. |
| 8,832,201 B2 | 9/2014 | Wall |
| 8,832,552 B2 | 9/2014 | Arrasvuori et al. |
| 8,839,327 B2 | 9/2014 | Amento et al. |
| 8,874,677 B2 | 10/2014 | Rosen et al. |
| 8,890,926 B2 | 11/2014 | Tandon et al. |
| 8,892,999 B2 | 11/2014 | Nims et al. |
| 8,909,679 B2 | 12/2014 | Root et al. |
| 8,924,250 B2 | 12/2014 | Bates et al. |
| 8,963,926 B2 | 2/2015 | Brown et al. |
| 8,989,786 B2 | 3/2015 | Feghali |
| 8,995,433 B2 | 3/2015 | Rojas |
| 9,040,574 B2 | 5/2015 | Wang et al. |
| 9,055,416 B2 | 6/2015 | Rosen et al. |
| 9,086,776 B2 | 7/2015 | Ye et al. |
| 9,100,806 B2 | 8/2015 | Rosen et al. |
| 9,100,807 B2 | 8/2015 | Rosen et al. |
| 9,105,014 B2 | 8/2015 | Collet et al. |
| 9,191,776 B2 | 11/2015 | Root et al. |
| 9,204,252 B2 | 12/2015 | Root |
| 9,241,184 B2 | 1/2016 | Weerasinghe |
| 9,256,860 B2 | 2/2016 | Herger et al. |
| 9,298,257 B2 | 3/2016 | Hwang et al. |
| 9,314,692 B2 | 4/2016 | Konoplev et al. |
| 9,330,483 B2 | 5/2016 | Du et al. |
| 9,357,174 B2 | 5/2016 | Li et al. |
| 9,361,510 B2 | 6/2016 | Yao et al. |
| 9,378,576 B2 | 6/2016 | Bouaziz et al. |
| 9,402,057 B2 | 7/2016 | Kaytaz et al. |
| 9,412,192 B2 | 8/2016 | Mandel et al. |
| 9,443,227 B2 | 9/2016 | Evans et al. |
| 9,460,541 B2 | 10/2016 | Li et al. |
| 9,489,661 B2 | 11/2016 | Evans et al. |
| 9,489,760 B2 | 11/2016 | Li et al. |
| 9,491,134 B2 | 11/2016 | Rosen et al. |
| 9,503,845 B2 | 11/2016 | Vincent |
| 9,508,197 B2 | 11/2016 | Quinn et al. |
| 9,517,403 B1 | 12/2016 | Kim et al. |
| 9,544,257 B2 | 1/2017 | Ogundokun et al. |
| 9,576,400 B2 | 2/2017 | Van Os et al. |
| 9,589,357 B2 | 3/2017 | Li et al. |
| 9,592,449 B2 | 3/2017 | Barbalet et al. |
| 9,633,447 B2 | 4/2017 | Swaminathan et al. |
| 9,645,394 B2 | 5/2017 | Kinnebrew et al. |
| 9,648,376 B2 | 5/2017 | Chang et al. |
| 9,652,897 B2 | 5/2017 | Osborn et al. |
| 9,697,635 B2 | 7/2017 | Quinn et al. |
| 9,706,040 B2 | 7/2017 | Kadirvel et al. |
| 9,744,466 B2 | 8/2017 | Fujioka |
| 9,746,990 B2 | 8/2017 | Anderson et al. |
| 9,749,270 B2 | 8/2017 | Collet et al. |
| 9,792,714 B2 | 10/2017 | Li et al. |
| 9,839,844 B2 | 12/2017 | Dunstan et al. |
| 9,883,838 B2 | 2/2018 | Kaleal, III et al. |
| 9,898,849 B2 | 2/2018 | Du et al. |
| 9,911,073 B1 | 3/2018 | Spiegel et al. |
| 9,936,165 B2 | 4/2018 | Li et al. |
| 9,959,037 B2 | 5/2018 | Chaudhri et al. |
| 9,980,100 B1 | 5/2018 | Charlton et al. |
| 9,990,373 B2 | 6/2018 | Fortkort |
| 10,039,988 B2 | 8/2018 | Lobb et al. |
| 10,097,492 B2 | 10/2018 | Tsuda et al. |
| 10,116,598 B2 | 10/2018 | Tucker et al. |
| 10,134,296 B2 | 11/2018 | Anderson et al. |
| 10,155,168 B2 | 12/2018 | Blackstock et al. |
| 10,173,141 B1 | 1/2019 | Schindler et al. |
| 10,242,477 B1 | 3/2019 | Charlton et al. |
| 10,242,503 B2 | 3/2019 | McPhee et al. |
| 10,262,250 B1 | 4/2019 | Spiegel et al. |
| 10,325,416 B1 | 6/2019 | Scapel et al. |
| 10,362,219 B2 | 7/2019 | Wilson et al. |
| 10,475,225 B2 | 11/2019 | Park et al. |
| 10,504,266 B2 | 12/2019 | Blattner et al. |
| 10,573,048 B2 | 2/2020 | Ni et al. |
| 10,657,701 B2 | 5/2020 | Osman et al. |
| 10,740,978 B2 | 8/2020 | McPhee et al. |
| 10,984,575 B2 | 4/2021 | Assouline et al. |
| 11,210,834 B1 | 12/2021 | Chamdani et al. |
| 11,450,051 B2 | 9/2022 | Assouline et al. |
| 2002/0067362 A1 | 6/2002 | Agostino Nocera et al. |
| 2002/0135581 A1 | 9/2002 | Russell et al. |
| 2002/0169644 A1 | 11/2002 | Greene |
| 2004/0212630 A1 | 10/2004 | Hobgood et al. |
| 2005/0041842 A1 | 2/2005 | Frakes et al. |
| 2005/0162419 A1 | 7/2005 | Kim et al. |
| 2005/0206610 A1 | 9/2005 | Cordelli |
| 2006/0294465 A1 | 12/2006 | Ronen et al. |
| 2007/0113181 A1 | 5/2007 | Blattner et al. |
| 2007/0168863 A1 | 7/2007 | Blattner et al. |
| 2007/0176921 A1 | 8/2007 | Iwasaki et al. |
| 2007/0230747 A1 | 10/2007 | Dunko |
| 2007/0279419 A1 | 12/2007 | Seebach |
| 2008/0078758 A1 | 4/2008 | Shimura et al. |
| 2008/0158222 A1 | 7/2008 | Li et al. |
| 2009/0016617 A1 | 1/2009 | Bregman-amitai et al. |
| 2009/0055484 A1 | 2/2009 | Vuong et al. |
| 2009/0070688 A1 | 3/2009 | Gyorfi et al. |
| 2009/0099925 A1 | 4/2009 | Mehta et al. |
| 2009/0106672 A1 | 4/2009 | Burstrom |
| 2009/0158170 A1 | 6/2009 | Narayanan et al. |

(56) References Cited

U.S. PATENT DOCUMENTS

| | | |
|---|---|---|
| 2009/0160779 A1 | 6/2009 | Crockett et al. |
| 2009/0177976 A1 | 7/2009 | Bokor et al. |
| 2009/0202114 A1 | 8/2009 | Morin et al. |
| 2009/0265604 A1 | 10/2009 | Howard et al. |
| 2009/0300525 A1 | 12/2009 | Jolliff et al. |
| 2009/0303984 A1 | 12/2009 | Clark et al. |
| 2010/0011422 A1 | 1/2010 | Mason et al. |
| 2010/0023885 A1 | 1/2010 | Reville et al. |
| 2010/0115426 A1 | 5/2010 | Liu et al. |
| 2010/0162149 A1 | 6/2010 | Sheleheda et al. |
| 2010/0203968 A1 | 8/2010 | Gill et al. |
| 2010/0227682 A1 | 9/2010 | Reville et al. |
| 2010/0251101 A1 | 9/2010 | Haussecker et al. |
| 2010/0281432 A1 | 11/2010 | Geisner et al. |
| 2010/0302138 A1 | 12/2010 | Poot et al. |
| 2010/0302253 A1 | 12/2010 | Kipman et al. |
| 2011/0007079 A1 | 1/2011 | Perez et al. |
| 2011/0093780 A1 | 4/2011 | Dunn |
| 2011/0115798 A1 | 5/2011 | Nayar et al. |
| 2011/0148864 A1 | 6/2011 | Lee et al. |
| 2011/0161242 A1 | 6/2011 | Chung et al. |
| 2011/0183732 A1 | 7/2011 | Block et al. |
| 2011/0202598 A1 | 8/2011 | Evans et al. |
| 2011/0216060 A1 | 9/2011 | Weising et al. |
| 2011/0239136 A1 | 9/2011 | Goldman et al. |
| 2012/0038628 A1 | 2/2012 | Corazza et al. |
| 2012/0113106 A1 | 5/2012 | Choi et al. |
| 2012/0124458 A1 | 5/2012 | Cruzada |
| 2012/0130717 A1 | 5/2012 | Xu et al. |
| 2012/0147014 A1 | 6/2012 | Lee |
| 2012/0188257 A1 | 7/2012 | Girard |
| 2012/0194549 A1 | 8/2012 | Osterhout et al. |
| 2012/0209924 A1 | 8/2012 | Evans et al. |
| 2012/0214594 A1 | 8/2012 | Kirovski et al. |
| 2013/0021373 A1 | 1/2013 | Vaught et al. |
| 2013/0050258 A1 | 2/2013 | Liu et al. |
| 2013/0091206 A1 | 4/2013 | Moraes et al. |
| 2013/0103760 A1 | 4/2013 | Golding et al. |
| 2013/0127980 A1 | 5/2013 | Haddick et al. |
| 2013/0141434 A1 | 6/2013 | Sugden et al. |
| 2013/0201187 A1 | 8/2013 | Tong et al. |
| 2013/0249948 A1 | 9/2013 | Reitan |
| 2013/0257877 A1 | 10/2013 | Davis |
| 2013/0278631 A1 | 10/2013 | Border et al. |
| 2014/0028713 A1 | 1/2014 | Keating et al. |
| 2014/0043329 A1 | 2/2014 | Wang et al. |
| 2014/0055554 A1 | 2/2014 | Du et al. |
| 2014/0078176 A1 | 3/2014 | Kim et al. |
| 2014/0125678 A1 | 5/2014 | Wang et al. |
| 2014/0129343 A1 | 5/2014 | Finsler et al. |
| 2014/0176608 A1 | 6/2014 | Boysen et al. |
| 2014/0253431 A1 | 9/2014 | Gossweiler, III et al. |
| 2014/0282223 A1 | 9/2014 | Bastien et al. |
| 2014/0321702 A1 | 10/2014 | Schmalstieg |
| 2014/0331149 A1 | 11/2014 | Labey |
| 2014/0351758 A1 | 11/2014 | Yoshida |
| 2015/0042663 A1 | 2/2015 | Mandel et al. |
| 2015/0098614 A1 | 4/2015 | Gee et al. |
| 2015/0154782 A1 | 6/2015 | Geisner et al. |
| 2015/0206349 A1 | 7/2015 | Rosenthal et al. |
| 2015/0262029 A1 | 9/2015 | Pirchheim et al. |
| 2015/0264304 A1 | 9/2015 | Chastney et al. |
| 2015/0269783 A1 | 9/2015 | Yun |
| 2015/0286829 A1 | 10/2015 | Amacker et al. |
| 2015/0309563 A1 | 10/2015 | Connor |
| 2015/0371447 A1 | 12/2015 | Yasutake |
| 2016/0025978 A1 | 1/2016 | Mallinson |
| 2016/0063600 A1 | 3/2016 | Wuang |
| 2016/0109940 A1 | 4/2016 | Lyren et al. |
| 2016/0134840 A1 | 5/2016 | Mcculloch |
| 2016/0171739 A1 | 6/2016 | Anderson et al. |
| 2016/0202755 A1 | 7/2016 | Connor |
| 2016/0210780 A1 | 7/2016 | Paulovich et al. |
| 2016/0234149 A1 | 8/2016 | Tsuda et al. |
| 2016/0247309 A1 | 8/2016 | Li et al. |
| 2016/0267699 A1 | 9/2016 | Borke et al. |
| 2016/0330522 A1 | 11/2016 | Newell et al. |
| 2016/0360115 A1 | 12/2016 | Rim |
| 2017/0038829 A1 | 2/2017 | Lanier et al. |
| 2017/0039986 A1 | 2/2017 | Lanier et al. |
| 2017/0069134 A1 | 3/2017 | Shapira et al. |
| 2017/0080346 A1 | 3/2017 | Abbas |
| 2017/0084070 A1 | 3/2017 | Chamdani et al. |
| 2017/0087473 A1 | 3/2017 | Siegel et al. |
| 2017/0090747 A1 | 3/2017 | Dash |
| 2017/0113140 A1 | 4/2017 | Blackstock et al. |
| 2017/0118145 A1 | 4/2017 | Aittoniemi et al. |
| 2017/0131781 A1 | 5/2017 | Buban |
| 2017/0178272 A1 | 6/2017 | Lashkari et al. |
| 2017/0199855 A1 | 7/2017 | Fishbeck |
| 2017/0206695 A1 | 7/2017 | Kim et al. |
| 2017/0221272 A1 | 8/2017 | Li et al. |
| 2017/0229153 A1 | 8/2017 | Moore et al. |
| 2017/0235848 A1 | 8/2017 | Van Deusen et al. |
| 2017/0255450 A1 | 9/2017 | Mullins et al. |
| 2017/0287060 A1 | 10/2017 | Choi et al. |
| 2017/0310934 A1 | 10/2017 | Du et al. |
| 2017/0312634 A1 | 11/2017 | Ledoux et al. |
| 2017/0329488 A1 | 11/2017 | Welker et al. |
| 2017/0361225 A1 | 12/2017 | Goslin et al. |
| 2018/0040166 A1 | 2/2018 | Jayaraj et al. |
| 2018/0047200 A1 | 2/2018 | O'hara et al. |
| 2018/0061072 A1 | 3/2018 | Benezra et al. |
| 2018/0082430 A1 | 3/2018 | Sharma et al. |
| 2018/0095542 A1 | 4/2018 | Mallinson |
| 2018/0108179 A1 | 4/2018 | Tomlin et al. |
| 2018/0113587 A1 | 4/2018 | Allen et al. |
| 2018/0114365 A1 | 4/2018 | Egri et al. |
| 2018/0115503 A1 | 4/2018 | Baldwin et al. |
| 2018/0143950 A1 | 5/2018 | Al-arnaouti et al. |
| 2018/0197343 A1 | 7/2018 | Hare et al. |
| 2018/0210628 A1 | 7/2018 | Mcphee et al. |
| 2018/0253897 A1 | 9/2018 | Satake |
| 2018/0285647 A1 | 10/2018 | Chen et al. |
| 2018/0315076 A1 | 11/2018 | Andreou |
| 2018/0315133 A1 | 11/2018 | Brody et al. |
| 2018/0315134 A1 | 11/2018 | Amitay et al. |
| 2018/0322680 A1* | 11/2018 | McElmurray ........... G06T 11/60 |
| 2018/0349451 A1 | 12/2018 | O'connell et al. |
| 2019/0001223 A1 | 1/2019 | Blackstock et al. |
| 2019/0004688 A1 | 1/2019 | Bowen |
| 2019/0011703 A1 | 1/2019 | Robaina et al. |
| 2019/0038187 A1 | 2/2019 | Latella, Jr. |
| 2019/0057616 A1 | 2/2019 | Cohen et al. |
| 2019/0107991 A1 | 4/2019 | Spivack et al. |
| 2019/0188920 A1 | 6/2019 | Mcphee et al. |
| 2019/0196663 A1 | 6/2019 | Monastyrshyn et al. |
| 2019/0255419 A1 | 8/2019 | Reilly et al. |
| 2019/0304189 A1 | 10/2019 | Falstrup et al. |
| 2019/0369836 A1 | 12/2019 | Faulkner et al. |
| 2019/0385374 A1 | 12/2019 | Kamhi et al. |
| 2019/0385378 A1 | 12/2019 | Bastian et al. |
| 2020/0066014 A1 | 2/2020 | Mehta et al. |
| 2020/0074738 A1 | 3/2020 | Hare et al. |
| 2020/0105006 A1 | 4/2020 | Karsch et al. |
| 2020/0105041 A1 | 4/2020 | Garofalo et al. |
| 2020/0134898 A1 | 4/2020 | Sheth et al. |
| 2020/0202632 A1 | 6/2020 | Goodrich et al. |
| 2020/0241299 A1 | 7/2020 | Nuber et al. |
| 2020/0241729 A1 | 7/2020 | Schneider et al. |
| 2020/0250874 A1 | 8/2020 | Assouline et al. |
| 2020/0265234 A1 | 8/2020 | Lee et al. |
| 2020/0327734 A1 | 10/2020 | Goodrich et al. |
| 2020/0341580 A1 | 10/2020 | Rosenbaum et al. |
| 2021/0150806 A1 | 5/2021 | Guler et al. |
| 2021/0166459 A1 | 6/2021 | Miller, IV |
| 2021/0201002 A1 | 7/2021 | Watanabe et al. |
| 2021/0209825 A1 | 7/2021 | Assouline et al. |
| 2021/0298868 A1 | 9/2021 | Rydberg |
| 2021/0383607 A1 | 12/2021 | Meng et al. |
| 2022/0028178 A1 | 1/2022 | Price et al. |
| 2022/0130115 A1 | 4/2022 | Assouline et al. |
| 2022/0156999 A1 | 5/2022 | Assouline et al. |

(56) References Cited

U.S. PATENT DOCUMENTS

| | | | |
|---|---|---|---|
| 2022/0157000 | A1 | 5/2022 | Assouline et al. |
| 2022/0157025 | A1 | 5/2022 | Assouline et al. |
| 2022/0383577 | A1 | 12/2022 | Assouline et al. |

FOREIGN PATENT DOCUMENTS

| | | | |
|---|---|---|---|
| CN | 110168478 | A | 8/2019 |
| DE | 102018207518 | | 11/2019 |
| EP | 2184092 | A2 | 5/2010 |
| JP | 2001230801 | A | 8/2001 |
| JP | 5497931 | B2 | 3/2014 |
| KR | 101445263 | B1 | 9/2014 |
| WO | WO-2003094072 | A1 | 11/2003 |
| WO | WO-2004095308 | A1 | 11/2004 |
| WO | WO-2006107182 | A1 | 10/2006 |
| WO | WO-2007134402 | A1 | 11/2007 |
| WO | WO-2012139276 | A1 | 10/2012 |
| WO | WO-2013027893 | A1 | 2/2013 |
| WO | WO-2013152454 | A1 | 10/2013 |
| WO | WO-2013166588 | A1 | 11/2013 |
| WO | WO-2014031899 | A1 | 2/2014 |
| WO | WO-2014194439 | A1 | 12/2014 |
| WO | WO-2016090605 | A1 | 6/2016 |
| WO | WO-2018081013 | A1 | 5/2018 |
| WO | WO-2018102562 | A1 | 6/2018 |
| WO | WO-2018129531 | | 7/2018 |
| WO | WO-2018129531 | A1 | 7/2018 |
| WO | WO-2019089613 | A1 | 5/2019 |
| WO | WO-2020047117 | A1 | 3/2020 |
| WO | WO-2020132541 | A1 | 6/2020 |
| WO | WO-2020163592 | A1 | 8/2020 |
| WO | 2022093939 | | 5/2022 |
| WO | 2022093958 | | 5/2022 |
| WO | 2022108805 | | 5/2022 |
| WO | 2022108806 | | 5/2022 |
| WO | 2022108807 | | 5/2022 |

OTHER PUBLICATIONS

"U.S. Appl. No. 17/081,178, Notice of Allowance dated Dec. 5, 2022", 9 pgs.
Mehta, Dushyant, et al., "VNect: Real-time 3D Human Pose Estimation with a Single RGB Camera", arxiv.org, Cornell University Library, (May 3, 2017), 13 pgs.
U.S. Appl. No. 17/212,555, filed Mar. 25, 2021, Body Pose Estimation.
U.S. Appl. No. 16/951,884, filed Nov. 18, 2020, Personalized Avatar Real-Time Motion Capture.
U.S. Appl. No. 16/951,921, filed Nov. 18, 2020, Body Animation Sharing and Remixing.
U.S. Appl. No. 16/951,939, filed Nov. 18, 2020, Real-Time Motion Transfer for Prosthetic Limbs.
"U.S. Appl. No. 17/081,178, Response filed Jun. 3, 2022 to Non Final Office Action dated Mar. 9, 2022", 10 pgs.
"U.S. Appl. No. 16/951,884, Notice of Allowance dated Jun. 8, 2022", 5 pgs.
"U.S. Appl. No. 16/951,884, Corrected Notice of Allowability dated Jun. 22, 2022", 2 pgs.
"U.S. Appl. No. 17/081,178, Notice of Allowance dated Aug. 17, 2022", 9 pgs.
"U.S. Appl. No. 16/951,939, Non Final Office Action dated Aug. 18, 2022", 16 pgs.
"U.S. Appl. No. 17/081,178, Supplemental Notice of Allowability dated Aug. 31, 2022", 2 pgs.
"U.S. Appl. No. 17/212,555, Notice of Allowance dated Sep. 1, 2022", 8 pgs.
"U.S. Appl. No. 16/951,921, Non Final Office Action dated Oct. 7, 2022", 27 pgs.
"U.S. Appl. No. 17/212,555, Corrected Notice of Allowability dated Sep. 22, 2022", 2 pgs.

"U.S. Appl. No. 16/269,312, Examiner Interview dated Jun. 24, 2020", 3 pgs.
"U.S. Appl. No. 16/269,312, Non Final Office Action dated Apr. 14, 2020", 18 pgs.
"U.S. Appl. No. 16/269,312, Notice of Allowance dated Aug. 19, 2020", 9 pgs.
"U.S. Appl. No. 16/269,312, Response filed Jun. 23, 2020 to Non Final Office Action dated Apr. 14, 2020", 10 pgs.
"International Application Serial No. PCT/US2020/017006, International Search Report dated Jul. 30, 2020", 6 pgs.
"International Application Serial No. PCT/US2020/017006, Invitation to Pay Additional Fees dated Jun. 2, 2020", 13 pgs.
"International Application Serial No. PCT/US2020/017006, Written Opinion dated Jul. 30, 2020", 12 pgs.
"Skeletal animation", Wikipedia, [Online] Retrieved from the Internet: <URL: https://en.wikipedia.org/w/index.php?title=Skeletal_animation&oldid=694599494>, (Dec. 10, 2015), 3 pgs.
Fieraru, Mihai, et al., "Learning to Refine Human Pose Estimation", IEEE/CVF Conference on Computer Vision and Pattern Recognition Workshops (CVPRW), (2018), 318-327.
Giaccone, P R, et al., "Foreground-background segmentation by cellular neural networks", IEEE 15th International Conference on Pattern Recognition (ICPR—2000), vol. 2, (2000), 438-441.
Kawai, Norihiko, et al., "Diminished Reality Based on Image Inpainting Considering Background Geometry", IEEE transactions on visualization and computer graphics, 22(3), (Mar. 1, 2016), 1236-1247.
Leyden, John, "This SMS will self-destruct in 40 seconds", [Online] Retrieved from the Internet: <URL: http://www.theregister.co.uk/2005/12/12/stealthtext/>, (Dec. 12, 2005), 1 pg.
Lipeng, KE, et al., "Multi-Scale Structure-Aware Network for Human Pose Estimation", Springer Nature Switzerland AG, ECCV 2018, LNCS 11206, (2018), 731-746.
Marto, Anabela G R, et al., "DinofelisAR Demo: Augmented Reality Based on Natural Features", 12th Iberian Conference on Information Systems and Technologies (CISTI), Lisbon, Portugal, (Jun. 2017), 6 pgs.
Mehta, Dushyant, et al., "VNect: Real-time 3D Human Pose Estimation with a Single RGB CdITISPd", arXiv:1705.01583v1 [cs.CV], (May 3, 2017), 13 pgs.
Nakajima, Yoshikatsu, et al., "Semantic Object Selection and Detection for Diminished Reality Based on SLAM with Viewpoint Class", IEEE International Symposium on Mixed and Augmented Reality Adjunct Proceedings, (2017), 338-343.
Park, Jong-Seung, et al., "Virtual Object Placement in Video for Augmented Reality", Advances in Multimedia Information Processing—PCM 2005: 6th Pacific Rim Conference on Multimedia, Jeju Island, KR, Proceedings (vol. 3767). Springer, Berlin, DE, (2005), 13-24.
Robinson, Ian, "Add 3D text to video footage", Adobe.com/Youtube video, [Online] Retrieved from the Internet: <URL: https://helpx.adobe.com/after-effects/how-to/add-3d-text-video-footage.html>, (Mar. 10, 2017), 360 pgs.; 15:22 min.
Salas-Morena, Renato F, et al., "Dense Planar SLAM", IEEE Intl. Symposium on Mixed and Augmented Reality (ISMAR), Munich, Germany, [Online] Retrieved from the Internet: <URL: http://www.doc.ic.ac.uk/'bglocker/pdfs/salas-moreno2014ismar.pdf>, (Sep. 2014), 8 pgs.
Schettini, R, et al., "A segmentation algorithm for color images", Pattern Recognition Letters, Elsevier, Amsterdam, NL, vol. 14, No. 6, (Jun. 1, 1993), 499-506.
Shohei, Mori, et al., "A survey of diminished reality: Techniques for visually concealing, eliminating, and seeing through real objects", IPSJ Transactions on Computer Vision and Applications, vol. 9, No. 1, (Jun. 28, 2017), 14 pgs.
"U.S. Appl. No. 16/951,884, Non Final Office Action dated Sep. 9, 2021", 14 pgs.
"U.S. Appl. No. 17/212,555, Non Final Office Action dated Oct. 4, 2021", 20 pgs.
"U.S. Appl. No. 16/951,884, Response filed Dec. 1, 2021 to Non Final Office Action dated Sep. 9, 2021", 11 pgs.
"U.S. Appl. No. 17/212,555, Response filed Jan. 3, 2022 to Non Final Office Action dated Oct. 4, 2021", 10 pgs.

(56) References Cited

OTHER PUBLICATIONS

"U.S. Appl. No. 16/951,884, Final Office Action dated Jan. 7, 2022", 15 pgs.
"International Application Serial No. PCT/US2021/056850, International Search Report dated Feb. 9, 2022", 5 pgs.
"International Application Serial No. PCT/US2021/056850, Written Opinion dated Feb. 9, 2022", 9 pgs.
"U.S. Appl. No. 16/951,884, Response filed Feb. 16, 2022 to Final Office Action dated Jan. 7, 2022", 10 pgs.
"U.S. Appl. No. 17/212,555, Final Office Action dated Mar. 2, 2022", 25 pgs.
"U.S. Appl. No. 16/951,884, Notice of Allowance dated Mar. 9, 2022", 5 pgs.
"U.S. Appl. No. 17/081,178, Non Final Office Action dated Mar. 9, 2022", 31 pgs.
"International Application Serial No. PCT/US2021/058800, International Search Report dated Feb. 18, 2022", 4 pgs.
"International Application Serial No. PCT/US2021/058800, Written Opinion dated Feb. 18, 2022", 6 pgs.
"International Application Serial No. PCT/US2021/056820, International Search Report dated Feb. 28, 2022", 4 pgs.
"International Application Serial No. PCT/US2021/056820, Written Opinion dated Feb. 28, 2022", 9 pgs.
"International Application Serial No. PCT/US2021/058816, International Search Report dated Mar. 3, 2022", 5 pgs.
"International Application Serial No. PCT/US2021/058816, Written Opinion dated Mar. 3, 2022", 15 pgs.
"International Application Serial No. PCT/US2021/058811, International Search Report dated Feb. 24, 2022", 5 pgs.
"International Application Serial No. PCT/US2021/058811, Written Opinion dated Feb. 24, 2022", 11 pgs.
"U.S. Appl. No. 17/212,555, Response filed Apr. 29, 2022 to Final Office Action dated Mar. 2, 2022", 9 pgs.
"U.S. Appl. No. 17/212,555, Notice of Allowance dated May 17, 2022", 8 pgs.
Cimen, Gokcen, "AR Poser: Automatically Augmenting Mobile Pictures with Digital Avatars Imitating Poses", 12th International Conference on Computer Graphics, Visualization, Computer Vision and Image Processing, (Jul. 18, 2018), 5 pgs.
Cimen, Gokcen, "Animation Models for Interactive AR Characters", Doctoral dissertation, Retrieved from the Internet: <URL:https://www.research-collection.ethz.ch/bitstream/handle/20.500.11850/372660/5/AnimationModelsforInteractiveARCharacters.pdf>, [retrieved on Feb. 15, 2022], (Jan. 1, 2019), 1-113.
Vogele, Anna, "Interactive steering of mesh animations", Computer Animation, Eurographics Association, P. 0. Box 16 Aire-La-Ville CH—1288 Switzerland, (Jul. 29, 2012), 53-58.
Yamane, Katsu, "Animating non-humanoid characters with human motion data", Computer Animation, Eurographics Association, P. 0. Box 16 Aire-La-Ville CH—1288 Switzerland, (Jul. 2, 2010), 169-178.
Yong, Du, "Hierarchical Recurrent Neural Network for Skeleton Based Action Recognition", IEEE Conference on Computer Vision and Pattern Recognition (CVPR), (Jun. 2015), 1110-1118.
"U.S. Appl. No. 16/269,312, Notice of Allowance dated Dec. 30, 2020", 9 pgs.
U.S. Appl. No. 16/269,312, filed Feb. 6, 2019, Body Pose Estimation.
U.S. Appl. No. 17/081,178, filed Oct. 27, 2020, Side-by-Side Character Animation From Realtime 3D Body Motion Capture.

* cited by examiner

ADAPTIVE SKELETAL JOINT SMOOTHING

CLAIM OF PRIORITY

This application claims the benefit of priority to U.S. Provisional Application Ser. No. 63/198,553, filed on Oct. 27, 2020, which is incorporated herein by reference in its entirety.

TECHNICAL FIELD

The present disclosure relates generally to tracking movement of a user in a video.

BACKGROUND

Image processing systems can be used to react to different actions users perform that are captured by a camera. Such systems can modify presentation of virtual objects or perform other application specific functions. Such systems can be subject to presentation problems due to environmental conditions, user actions, unanticipated visual interruption between a camera and the object being rendered, and the like. The presentation problems also arise due to failure to accurately detect user actions. This can cause a virtual object to disappear or otherwise behave erratically, or incorrect functions to be executed, which breaks the illusion of the virtual objects being present in the real world.

BRIEF DESCRIPTION OF THE DRAWINGS

In the drawings, which are not necessarily drawn to scale, like numerals may describe similar components in different views. To easily identify the discussion of any particular element or act, the most significant digit or digits in a reference number refer to the figure number in which that element is first introduced. Some embodiments are illustrated by way of example, and not limitation, in the figures of the accompanying drawings in which.

DETAILED DESCRIPTION

Figure 1:
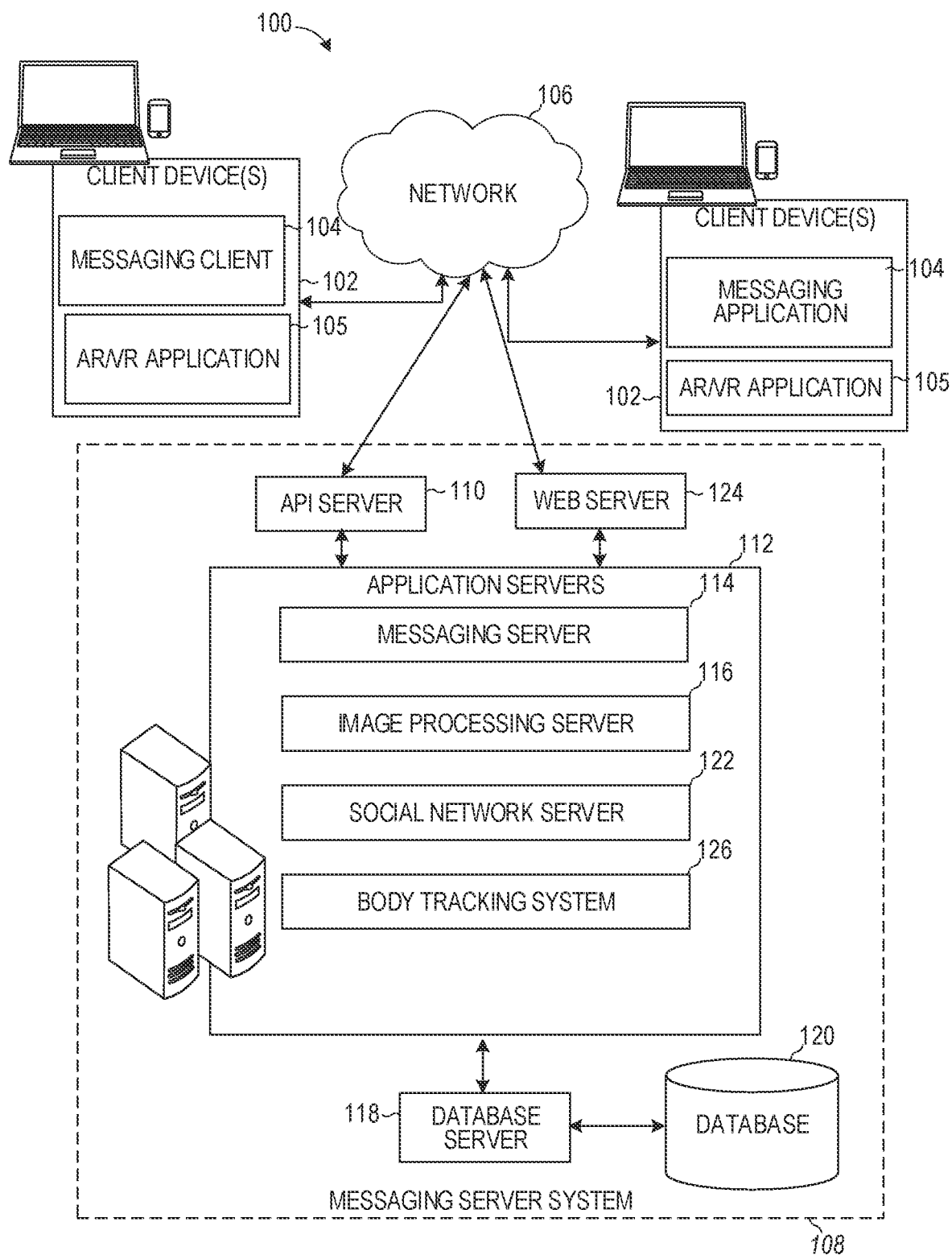
FIG. 1 is a block diagram showing an example messaging system for exchanging data (e.g., messages and associated content) over a network, according to example embodiments.

The description that follows includes systems, methods, techniques, instruction sequences, and computing machine program products that embody illustrative embodiments of the disclosure. In the following description, for the purposes of explanation, numerous specific details are set forth in order to provide an understanding of various embodiments. It will be evident, however, to those skilled in the art, that embodiments may be practiced without these specific details. In general, well-known instruction instances, protocols, structures, and techniques are not necessarily shown in detail.

Typically, virtual reality (VR) and augmented reality (AR) systems display avatars representing a given user by capturing an image of the user and, in addition, obtaining a depth map using a depth sensor of the real-world human body depicted in the image. By processing the depth map and the image together, the VR and AR systems can detect and mimic or react to actions performed by the user. While such systems work well for presenting avatars of a user and reacting to actions performed by the user, such as modifying virtual objects or performing application functions, the need for a depth sensor limits the scope of their applications. This is because adding depth sensors to user devices for the purpose of displaying avatars or performing actions in response to user-detected poses increases the overall cost and complexity of the devices, making them less attractive.

Certain systems attempt to detect user actions, such as poses, that are received in a video based on joint positions of the body of the user depicted in the image. Such systems rely on predetermined angles of various joint positions to be specified. These systems compute angles of the joint positions detected in an image in real-time for comparison with the predetermined angles in order to detect a given pose. Inputting such angles requires a certain level of skill and consumes a great deal of time, especially when a large subset of poses are being tracked. This reduces the scalability of the systems and increases the overall amount of resources such systems consume. Even still, tracking movement of the joints across a set of video frames can be noisy. Namely, the movement of a pair of joints may not be accurately determined and detected across a set of adjacent frames. This also results in the corresponding movement appearing to be jumpy. Some systems apply a single smoothing filter to the joints collectively. However, sometimes smoothing may not be needed at all and application of the smoothing filter requires a large amount of processing and memory resources which slows down the overall detection system. This makes such systems difficult to implement and apply on real-time images or videos that are being received.

The disclosed embodiments improve the efficiency of using the electronic device by applying smoothing filters to skeletal joints of a user's body in a video independently on separate pairs or sets of joints. This way, if one set of joints requires more smoothing than another set of joints, the smoothing filters can be adapted to apply different amounts of smoothing to the different sets of joints. This improves the overall responsiveness of the filters that are applied to smooth joints of a person tracked in a video, as unnecessary smoothing can be reduced or avoided altogether. In particular, the disclosed embodiments receive a video that includes a depiction of a body of a user and detect a plurality of skeletal joints of the body depicted in the video. The disclosed embodiments track movement of the plurality of skeletal joints across a set of frames of the video and smooth the movement of a first set of the plurality of skeletal joints between frames in the first set of frames independently of (or separately from) smoothing movement of a second set of the plurality of skeletal joints in the first set of frames.

Specifically, noise representing movement of the joint or joints of a person in a video can be measured and multiple smoothing filters (e.g., with different smoothing characteristics) can be applied in parallel to smooth movement of a given joint or set of joints based on the measured noise. Namely, if the noise exceeds a threshold value, more weight can be applied to the output of a smoothing filter that has a first characteristic (e.g., an aggressive motion filter) to smooth movement of a given joint than the weight applied to the output of a smoothing filter that has a second characteristic (e.g., a soft motion filter) to smooth movement of the given joint. The weighted outputs of the two smoothing filters can be aggregated to smooth overall motion of the given joint. In this way, the responsiveness of motion filters being applied to smooth movement of the joints can be controlled (e.g., increased or decreased) without applying too much smoothing to the movement (e.g., oversmoothing) or an insufficient amount of smoothing (e.g., undersmoothing). For example, if there is a measure of noise that exceeds a threshold, an aggressive filter can be weighted more heavily than a soft filter which decreases the responsiveness but increases smoothing. If there is a measure of noise that is less than a threshold, an aggressive filter can be weighted less heavily than a soft filter which increases the responsiveness but decreases smoothing.

Virtual objects (e.g., a three-dimensional object, such as a 3D caption, emoji, character, avatar, animation, looping animation of a personalized avatar or character, looping or non-looping animated graphic such as a dancing hot dog, a stylized word with animation, and so forth) can be generated directly from a single red, green, and blue (RGB) video depicting the real-world user's body in response to tracking the skeletal joints and smoothing the sets of joints separately. The disclosed embodiments generate the virtual object without also obtaining a depth map of the real-world user's body. This enables a user device with a simple RGB camera (without a depth sensor) to accurately and quickly render an animated virtual object based on the real-world user's body within the VR or AR application, allowing the user to interact with the VR or AR content in a more realistic environment.

Networked Computing Environment

FIG. 1 is a block diagram showing an example messaging system 100 for exchanging data (e.g., messages and associated content) over a network. The messaging system 100 includes multiple instances of a client device 102, each of which hosts a number of applications, including a messaging client 104 and an AR/VR application 105. Each messaging client 104 and AR/VR application 105 is communicatively coupled to other instances of the messaging client 104 and AR/VR application 105 and a messaging server system 108 via a network 106 (e.g., the Internet).

A messaging client 104 and AR/VR application 105 are able to communicate and exchange data with another messaging client 104 and AR/VR application 105 and with the messaging server system 108 via the network 106. The data exchanged between messaging client 104, and between a messaging client 104 and the messaging server system 108, includes functions (e.g., commands to invoke functions) as well as payload data (e.g., text, audio, video or other multimedia data).

AR/VR application 105 is an application that includes a set of functions that allow the client device 102 to access body tracking system 126. In some implementations, the AR/VR application 105 is a component or a feature that is part of the messaging client 104. AR/VR application 105 uses an RGB camera to capture one or more images (e.g., a video) of a user's real-world body. The AR/VR application 105 applies one or more trained machine learning techniques on the captured images of the body to detect skeletal joint positions of the body. The AR/VR application 105 generates an outline of the user's body, such as by drawing a line that connects the different skeletal joint positions that are detected. The AR/VR application 105 tracks movement of the skeletal joints across a set of video frames. For example, the AR/VR application 105 selects pairs of adjacent joints (e.g., a shoulder joint and an elbow joint pair and a hip joint and a knee joint pair).

The AR/VR application 105 tracks movement of the pair of joints across a set of video frames and measures noise in each of the pair of joints that are detected across the set of frames. Based on the measured amount of noise, the AR/VR application 105 modifies a smoothing parameter of one or more smoothing filters that are applied to the different pairs of joints. In one example, a first smoothing parameter is applied to a first set of filters applied to a first pair of joints and a second smoothing parameter is applied to a second set of filters applied to a second pair of joints. The first smoothing parameter may cause the first set of filters to apply a greater amount of smoothing (e.g., because of a greater than a threshold value amount of noise was detected) for the first pair of skeletal joints in a subsequent set of frames or the current set of frames of the video. The second smoothing parameter may cause the second set of filters to apply a smaller amount of smoothing (e.g., because of a less than the threshold value amount of noise was detected) for the second pair of skeletal joints in the current or subsequent set of frames of the video. In this way, a different amount of smoothing is applied on a per pair of joints or per set of joints basis as a video depicting a person is received and captured in real-time. In another example, multiple smoothing filters can be applied in parallel to the same set of joints but the outputs of the smoothing filters can be weighted and summed on the basis of an amount of noise in the movement of the set of joints across a window of frames. Namely, the weights applied to the smoothing filters applied to the same set of joints can be controlled and varied based on how much noise is measured in movement of the set of joints across the set of frames.

In some embodiments, the AR/VR application 105 detects joint positions of a body depicted in a captured RGB image directly from the captured RGB image by obtaining a first trained machine learning technique from local or remote storage. The first trained machine learning technique processes the captured RGB image to extract one or more features from the RGB image that correspond to the body depicted in the captured RGB image. The features are analyzed to identify one or more skeletal joints and their respective alignment relative to one another. Specifically, the features are analyzed to determine the joint positions of a specified set of skeletal joints. The AR/VR application 105 also obtains a second trained machine learning technique to process one or more previously captured frames (e.g., 1-2 seconds of video frames that immediately precede the RGB image) to estimate or predict skeletal joint positions for a subsequent frame. A threshold number of seconds of video frames (which may be user defined, previously specified, and/or dynamically determined) may continuously or periodically be stored in a buffer, such that the threshold number of seconds worth of video frames that precedes a current RGB image can be accessed by the second trained machine learning technique. The output or prediction of the skeletal joint positions of the second trained machine learning technique is used to filter or improve the skeletal joint positions identified by the first trained machine learning technique. In some cases, the second trained machine learning technique processes the skeletal joint positions identified by the first trained machine learning technique together with the previously captured frames to filter or improve the estimated skeletal joint positions. Techniques for detecting skeletal joint positions are described in greater detail in commonly-owned Assouline et al. U.S. patent application Ser. No. 16/710,980, filed Dec. 11, 2019, which is hereby incorporated by reference in its entirety.

The messaging server system 108 provides server-side functionality via the network 106 to a particular messaging client 104. While certain functions of the messaging system 100 are described herein as being performed by either a messaging client 104 or by the messaging server system 108, the location of certain functionality either within the messaging client 104 or the messaging server system 108 may be a design choice. For example, it may be technically preferable to initially deploy certain technology and functionality within the messaging server system 108 but to later migrate this technology and functionality to the messaging client 104 where a client device 102 has sufficient processing capacity.

The messaging server system 108 supports various services and operations that are provided to the messaging client 104. Such operations include transmitting data to, receiving data from, and processing data generated by the messaging client 104. This data may include message content, client device information, geolocation information, media augmentation and overlays, message content persistence conditions, social network information, and live event information, as examples. Data exchanges within the messaging system 100 are invoked and controlled through functions available via user interfaces (UIs) of the messaging client 104.

Turning now specifically to the messaging server system 108, an Application Program Interface (API) server 110 is coupled to, and provides a programmatic interface to, application servers 112, including body tracking system 126. The application servers 112 are communicatively coupled to a. database server 118, which facilitates access to a database 120 that stores data associated with messages processed by the application servers 112. Similarly, a web server 124 is coupled to the application servers 112, and provides web-based interfaces to the application servers 112. To this end, the web server 124 processes incoming network requests over the Hypertext Transfer Protocol (HTTP) and several other related protocols.

The Application Program Interface (API) server 110 receives and transmits message data (e.g., commands and message payloads) between the client device 102 and the application servers 112. Specifically, the Application Program Interface (API) server 110 provides a set of interfaces (e.g., routines and protocols) that can be called or queried by the messaging client 104 in order to invoke functionality of the application servers 112. The Application Program Interface (API) server 110 exposes various functions supported by the application servers 112, including account registration, login functionality, the sending of messages, via the application servers 112, from a particular messaging client 104 to another messaging client 104, the sending of media files (e.g., images or video) from a messaging client 104 to a messaging server 114, and for possible access by another messaging client 104, the settings of a collection of media data (e.g., story), the retrieval of a list of friends of a user of a client device 102, the retrieval of such collections, the retrieval of messages and content, the addition and deletion of entities (e.g., friends) to an entity graph (e.g., a social graph), the location of friends within a social graph, and opening an application event (e.g., relating to the messaging client 104).

The application servers 112 host a number of server applications and subsystems, including for example a messaging server 114, an image processing server 116, body tracking system 126, and a social network server 122. The messaging server 114 implements a number of message processing technologies and functions, particularly related to the aggregation and other processing of content (e.g., textual and multimedia content) included in messages received from multiple instances of the messaging client 104. As will be described in further detail, the text and media content from multiple sources may be aggregated into collections of content (e.g., called stories or galleries). These collections are then made available to the messaging client 104. Other processor- and memory-intensive processing of data may also be performed server-side by the messaging server 114, in view of the hardware requirements for such processing.

The application servers 112 also include an image processing server 116 that is dedicated to performing various image processing operations, typically with respect to images or video within the payload of a message sent from or received at the messaging server 114.

Figure 3:
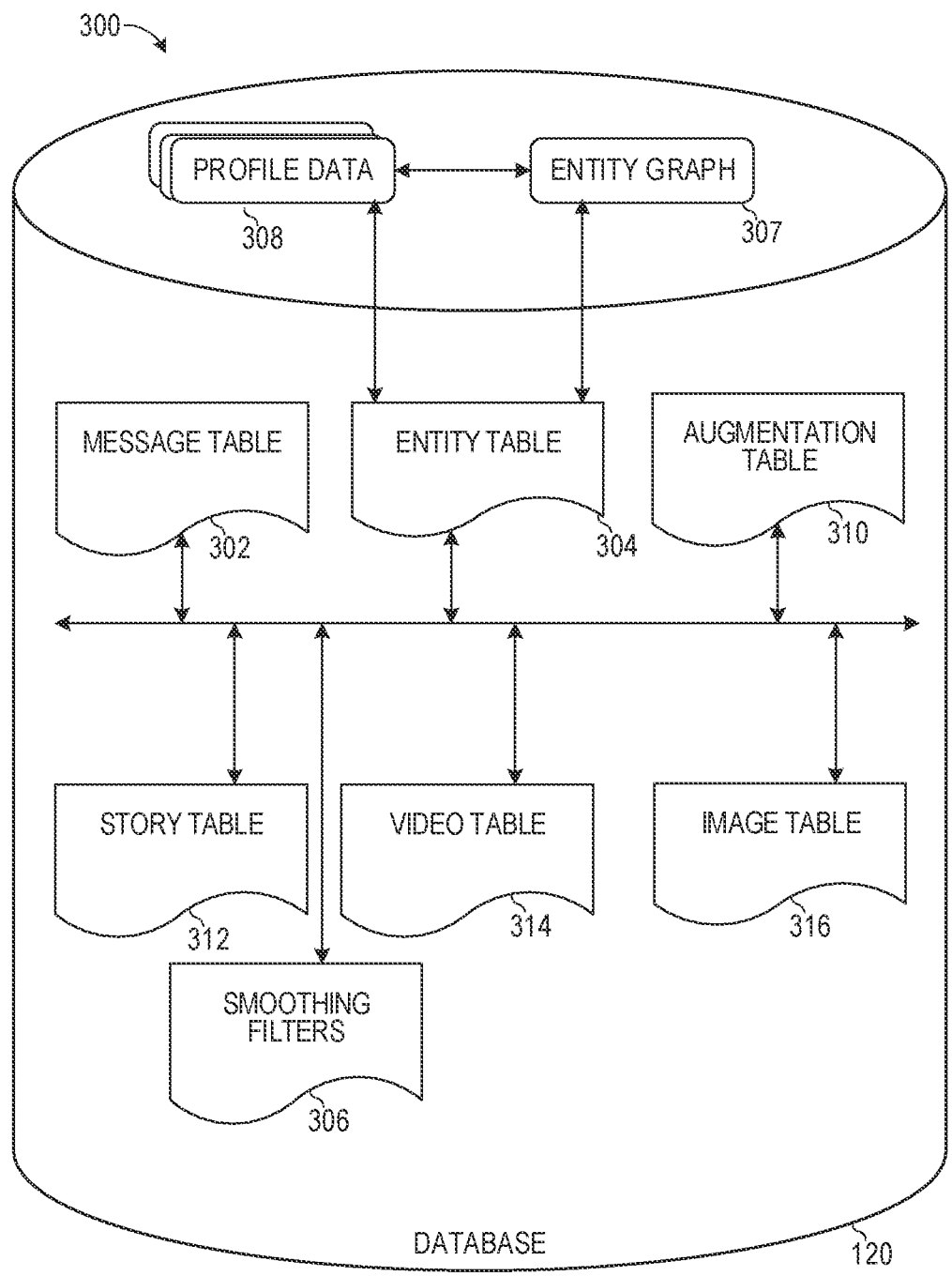
FIG. 3 is a schematic diagram illustrating data which may be stored in the database of a messaging server system, according to example embodiments.

The social network server 122 supports various social networking functions and services and makes these functions and services available to the messaging server 114. To this end, the social network server 122 maintains and accesses an entity graph 306 (as shown in FIG. 3) within the database 120. Examples of functions and services supported by the social network server 122 include the identification of other users of the messaging system 100 with which a particular user has relationships or is "following," and also the identification of other entities and interests of a particular user.

System Architecture

Figure 2:
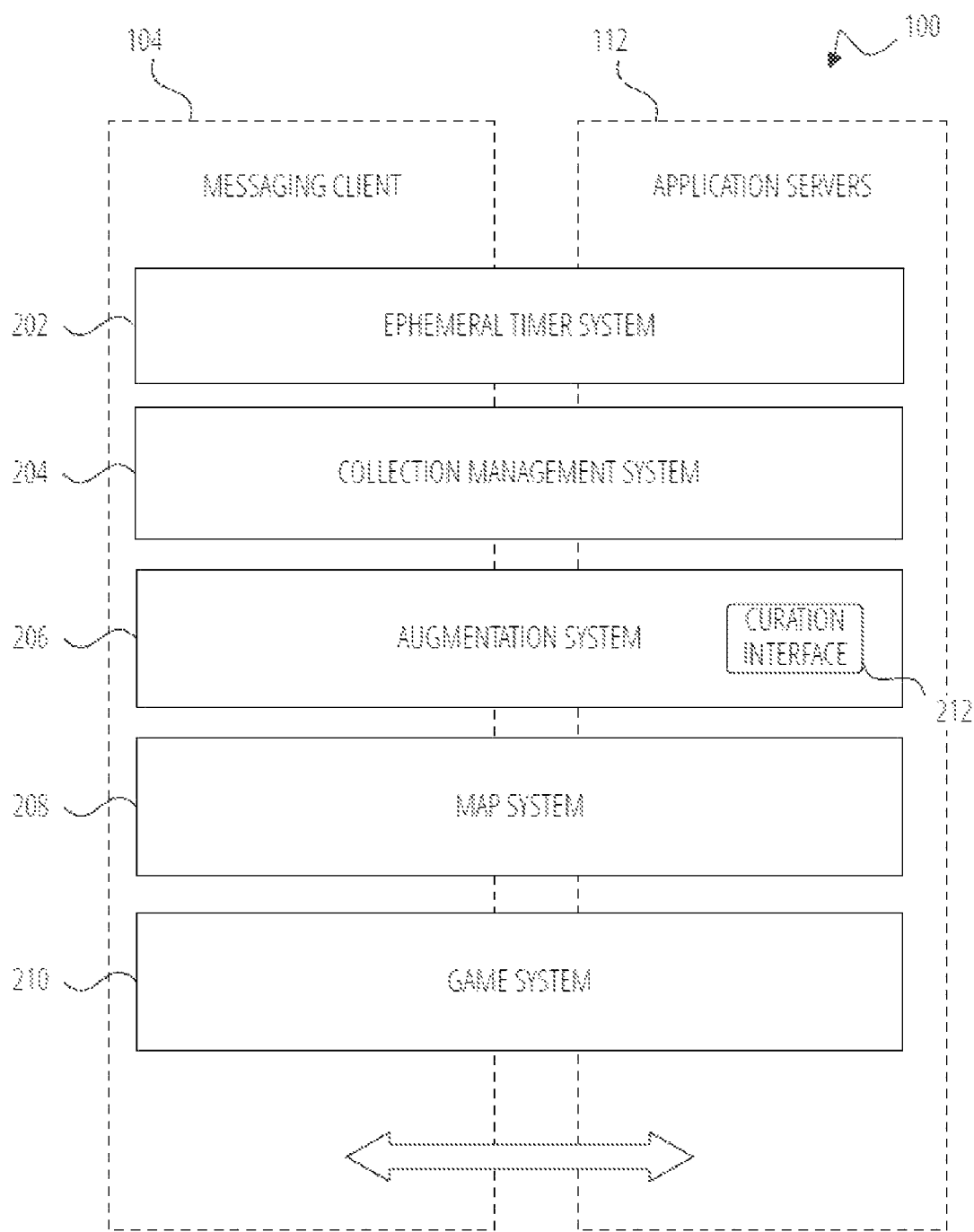
FIG. 2 is a block diagram illustrating further details regarding the messaging system of FIG. 1, according to example embodiments.

FIG. 2 is a block diagram illustrating further details regarding the messaging system 100, according to some examples. Specifically, the messaging system 100 is shown to comprise the messaging client 104 and the application servers 112. The messaging system 100 embodies a number of subsystems, which are supported on the client side by the messaging client 104 and on the sever side by the application servers 112. These subsystems include, for example, an ephemeral timer system 202, a collection management system 204, an augmentation system 206, a map system 208, and a game system 210. In some implementations, augmentation system 206 implements some or all of the functionality of the body tracking system 126.

The ephemeral timer system 202 is responsible for enforcing the temporary or time-limited access to content by the messaging client 104 and the messaging server 114. The ephemeral timer system 202 incorporates a number of timers that, based on duration and display parameters associated with a message, or collection of messages (e.g., a story), selectively enable access (e.g., for presentation and display)

to messages and associated content via the messaging client 104. Further details regarding the operation of the ephemeral timer system 202 are provided below.

The collection management system 204 is responsible for managing sets or collections of media (e.g., collections of text, image video, and audio data). A collection of content (e.g., messages, including images, video, text, and audio) may be organized into an "event gallery" or an "event story." Such a collection may be made available for a specified time period, such as the duration of an event to which the content relates. For example, content relating to a music concert may be made available as a "story" for the duration of that music concert. The collection management system 204 may also be responsible for publishing an icon that provides notification of the existence of a particular collection to the user interface of the messaging client 104.

The collection management system 204 furthermore includes a curation interface 212 that allows a collection manager to manage and curate a particular collection of content. For example, the curation interface 212 enables an event organizer to curate a collection of content relating to a specific event (e.g., delete inappropriate content or redundant messages). Additionally, the collection management system 204 employs machine vision (or image recognition technology) and content rules to automatically curate a content collection. in certain examples, compensation may be paid to a user for the inclusion of user-generated content into a collection. In such cases, the collection management system 204 operates to automatically make payments to such users for the use of their content.

The augmentation system 206 provides various functions that enable a user to augment (e.g., annotate or otherwise modify or edit) media content associated with a message. For example, the augmentation system 206 provides functions related to the generation and publishing of media overlays for messages processed by the messaging system 100. The augmentation system 206 operatively supplies a media overlay or augmentation (e.g., an image filter) to the messaging client 104 based on a geolocation of the client device 102. In another example, the augmentation system 206 operatively supplies a media overlay to the messaging client 104 based on other information, such as social network information of the user of the client device 102. A media overlay may include audio and visual content and visual effects. Examples of audio and visual content include pictures, texts, logos, animations, and sound effects. An example of a visual effect includes color overlaying. The audio and visual content or the visual effects can be applied to a media content item (e.g., a photo) at the client device 102. For example, the media overlay may include text or image that can be overlaid on top of a photograph taken by the client device 102. In another example, the media overlay includes an identification of a location overlay (e.g., Venice Beach), a name of a live event, or a name of a merchant overlay (e.g., Beach Coffee House). In another example, the augmentation system 206 uses the geolocation of the client device 102 to identify a media overlay that includes the name of a merchant at the geolocation of the client device 102. The media overlay may include other indicia associated with the merchant. The media overlays may be stored in the database 120 and accessed through the database server 118.

In some cases, the body tracking system 126 or portions of the body tracking system 126 can be implemented by or included in the augmentation system 206.

In some examples, the augmentation system 206 provides a user-based publication platform that enables users to select a geolocation on a map and upload content associated with the selected geolocation. The user may also specify circumstances under which a particular media overlay should be offered to other users. The augmentation system 206 generates a media overlay that includes the uploaded content and associates the uploaded content with the selected geolocation.

In other examples, the augmentation system 206 provides a merchant-based publication platform that enables merchants to select a particular media overlay associated with a geolocation via a bidding process. For example, the augmentation system 206 associates the media overlay of the highest bidding merchant with a corresponding geolocation for a predefined amount of time.

The map system 208 provides various geographic location functions, and supports the presentation of map-based media content and messages by the messaging client 104. For example, the map system 208 enables the display of user icons or avatars (e.g., stored in profile data 308) on a map to indicate a current or past location of "friends" of a user, as well as media content (e.g., collections of messages including photographs and videos) generated by such friends, within the context of a map. For example, a message posted by a user to the messaging system 100 from a specific geographic location may be displayed within the context of a map at that particular location to "friends" of a specific user on a map interface of the messaging client 104. A user can furthermore share his or her location and status information (e.g., using an appropriate status avatar) with other users of the messaging system 100 via the messaging client 104, with this location and status information being similarly displayed within the context of a map interface of the messaging client 104 to selected users.

The game system 210 provides various gaming functions within the context of the messaging client 104. The messaging client 104 provides a game interface providing a list of available games that can be launched by a user within the context of the messaging client 104, and played with other users of the messaging system 100. The messaging system 100 further enables a particular user to invite other users to participate in the play of a specific game, by issuing invitations to such other users from the messaging client 104. The messaging client 104 also supports both the voice and text messaging (e.g., chats) within the context of gameplay, provides a leaderboard for the games, and also supports the provision of in-game rewards (e.g., coins and items).

Data Architecture

FIG. 3 is a schematic diagram illustrating data structures 300, which may be stored in the database 120 of the messaging server system 108, according to certain examples. While the content of the database 120 is shown to comprise a number of tables, it will be appreciated that the data could be stored in other types of data structures (e.g., as an object-oriented database).

The database 120 includes message data stored within a message table 302. This message data includes, for any particular message, at least message sender data, message recipient (or receiver) data, and a payload. Further details regarding information that may be included in a message, and included within the message data stored in the message table 302, is described below with reference to FIG. 4.

An entity table 304 stores entity data, and is linked (e.g., referentially) to an entity graph 306 and profile data 308. Entities for which records are maintained within the entity table 304 may include individuals, corporate entities, organizations, objects, places, events, and so forth. Regardless of entity type, any entity regarding which the messaging server system 108 stores data may be a recognized entity. Each entity is provided with a unique identifier, as well as an entity type identifier (not shown).

The entity graph 306 stores information regarding relationships and associations between entities. Such relationships may be social, professional (e.g., work at a common corporation or organization) interest-based or activity-based, merely for example.

The profile data 308 stores multiple types of profile data about a particular entity. The profile data 308 may be selectively used and presented to other users of the messaging system 100, based on privacy settings specified by a particular entity. Where the entity is an individual, the profile data 308 includes, for example, a user name, telephone number, address, settings (e.g., notification and privacy settings), as well as a user-selected avatar representation (or collection of such avatar representations). A particular user may then selectively include one or more of these avatar representations within the content of messages communicated via the messaging system 100, and on map interfaces displayed by messaging clients 104 to other users. The collection of avatar representations may include "status avatars," which present a graphical representation of a status or activity that the user may select to communicate at a particular time.

Where the entity is a group, the profile data 308 for the group may similarly include one or more avatar representations associated with the group, in addition to the group name, members, and various settings (e.g., notifications) for the relevant group.

The database 120 also stores augmentation data, such as overlays or filters, in an augmentation table 310. The augmentation data is associated with and applied to videos (for which data is stored in a video table 314) and images (for which data is stored in an image table 316).

Filters, in one example, are overlays that are displayed as overlaid on an image or video during presentation to a recipient user. Filters may be of various types, including user-selected filters from a set of filters presented to a sending user by the messaging client 104 when the sending user is composing a message. Other types of filters include geolocation filters (also known as geo-filters), which may be presented to a sending user based on geographic location. For example, geolocation filters specific to a neighborhood or special location may be presented within a user interface by the messaging client 104, based on geolocation information determined by a Global Positioning System (GPS) unit of the client device 102.

Another type of filter is a data filter, which may be selectively presented to a sending user by the messaging client 104, based on other inputs or information gathered by the client device 102 during the message creation process. Examples of data filters include current temperature at a specific location, a current speed at which a sending user is traveling, battery life for a client device 102, or the current time.

Other augmentation data that may be stored within the image table 316 includes augmented reality content items (e.g., corresponding to applying lenses or augmented reality experiences), An augmented reality content item may be a real-time special effect and sound that may be added to an image or a video.

Smoothing filters 306 stores a plurality of smoothing filters that are used by the body tracking system 126, The smoothing filters may apply different amounts or types of smoothing to the joints or set or pairs of joints to which they are applied. The smoothing filters may each include a parameter that adjusts the coefficients of the filters to increase or decrease the amount of smoothing applied by a given smoothing filter.

As described above, augmentation data includes augmented reality content items, overlays, image transformations, AR images, and similar terms that refer to modifications that may be applied to image data (e.g., videos or images). This includes real-time modifications, which modify an image as it is captured using device sensors (e.g., one or multiple cameras) of a client device 102 and then displayed on a screen of the client device 102 with the modifications. This also includes modifications to stored content, such as video clips in a gallery that may be modified. For example, in a client device 102. with access to multiple augmented reality content items, a user can use a single video clip with multiple augmented reality content items to see how the different augmented reality content items will modify the stored clip. For example, multiple augmented reality content items that apply different pseudorandom movement models can be applied to the same content by selecting different augmented reality content items for the content. Similarly, real-time video capture may be used with an illustrated modification to show how video images currently being captured by sensors of a client device 102 would modify the captured data. Such data may simply be displayed on the screen and not stored in memory, or the content captured by the device sensors may be recorded and stored in memory with or without the modifications (or both). In some systems, a preview feature can show how different augmented reality content items will look within different windows in a display at the same time. This can, for example, enable multiple windows with different pseudorandom animations to be viewed on a display at the same time.

Data and various systems using augmented reality content items or other such transform systems to modify content using this data can thus involve detection of objects (e.g., faces, hands, bodies, cats, dogs. surfaces, objects, etc.), tracking of such objects as they leave, enter, and move around the field of view in video frames, and the modification or transformation of such objects as they are tracked. In various embodiments, different methods for achieving such transformations may be used. Some examples may involve generating a three-dimensional mesh model of the object or objects, and using transformations and animated textures of the model within the video to achieve the transformation. In other examples, tracking of points on an object may be used to place an image or texture (which may be two-dimensional or three-dimensional) at the tracked position. In still further examples, neural network analysis of video frames may be used to place images, models, or textures in content (e.g., images or frames of video). Augmented reality content items thus refer both to the images, models, and textures used to create transformations in content, as well as to additional modeling and analysis information needed to achieve such transformations with object detection, tracking, and placement.

Real-time video processing can be performed with any kind of video data (e.g., video streams, video files, etc.) saved in a memory of a computerized system of any kind. For example, a user can load video files and save them in a memory of a device, or can generate a video stream using sensors of the device. Additionally, any objects can be processed using a computer animation model, such as a human's face and parts of a human body, animals, or non-living things such as chairs, cars, or other objects.

In some examples, when a particular modification is selected along with content to be transformed, elements to be transformed are identified by the computing device, and then detected and tracked if they are present in the frames of the video. The elements of the object are modified according to the request for modification, thus transforming the frames of the video stream. Transformation of frames of a video stream can be performed by different methods for different kinds of transformation. For example, for transformations of frames mostly referring to changing forms of objects' elements, characteristic points for each element of an object: are calculated (e.g., using an Active Shape Model (ASM) or other known methods). Then, a mesh based on the characteristic points is generated for each of the at least one element of the object. This mesh is used in the following stage of tracking the elements of the object in the video stream. In the process of tracking, the mentioned mesh for each element is aligned with a position of each element. Then, additional points are generated on the mesh. A set of first points is generated for each element based on a request for modification, and a set of second points is generated for each element based on the set of first points and the request for modification. Then, the frames of the video stream can be transformed by modifying the elements of the object on the basis of the sets of first and second points and the mesh. In such method, a background of the modified object can be changed or distorted as well by tracking and modifying the background.

In some examples, transformations changing some areas of an object using its elements can be performed by calculating characteristic points for each element of an object and generating a mesh based on the calculated characteristic points. Points are generated on the mesh, and then various areas based on the points are generated. The elements of the object are then tracked by aligning the area for each element with a position for each of the at least one element, and properties of the areas can be modified based on the request for modification, thus transforming the frames of the video stream. Depending on the specific request for modification, properties of the mentioned areas can be transformed in different ways. Such modifications may involve changing color of areas; removing at least some part of areas from the frames of the video stream; including one or more new objects into areas which are based on a request for modification; and modifying or distorting the elements of an area or object. In various embodiments, any combination of such modifications or other similar modifications may be used. For certain models to be animated, some characteristic points can be selected as control points to be used in determining the entire state-space of options for the model animation.

In some examples of a computer animation model to transform image data using face detection, the face is detected on an image with use of a specific face detection algorithm (e.g., Viola-Jones). Then, an Active Shape Model (ASM) algorithm is applied to the face region of an image to detect facial feature reference points.

In other examples, other methods and algorithms suitable for face detection can be used. For example, in some embodiments, features are located using a landmark, which represents a distinguishable point present in most of the images under consideration. For facial landmarks, for example, the location of the left eye pupil may be used. If an initial landmark is not identifiable (e.g., if a person has an eyepatch), secondary landmarks may be used. Such landmark identification procedures may be used for any such objects. In some examples, a set of landmarks forms a shape. Shapes can be represented as vectors using the coordinates of the points in the shape. One shape is aligned to another with a similarity transform (allowing translation, scaling, and rotation) that minimizes the average Euclidean distance between shape points. The mean shape is the mean of the aligned training shapes.

In some examples, a search for landmarks from the mean shape aligned to the position and size of the face determined by a global face detector is started. Such a search then repeats the steps of suggesting a tentative shape by adjusting the locations of shape points by template matching of the image texture around each point and then conforming the tentative shape to a global shape model until convergence occurs. In some systems, individual template matches are unreliable, and the shape model pools the results of the weak template matches to form a stronger overall classifier. The entire search is repeated at each level in an image pyramid, from coarse to fine resolution.

A transformation system can capture an image or video stream on a client device (e.g., the client device 102) and perform complex image manipulations locally on the client device 102 while maintaining a suitable user experience, computation time, and power consumption. The complex image manipulations may include size and shape changes, emotion transfers changing a face from a frown to a smile), state transfers (e.g., aging a subject, reducing apparent age, changing gender), style transfers, graphical element application, and any other suitable image or video manipulation implemented by a convolutional neural network that has been configured to execute efficiently on the client device 102.

In some examples, a computer animation model to transform image data can be used by a system where a user may capture an image or video stream of the user (e.g., a selfie) using a client device 102 having a neural network operating as part of a messaging client 104 operating on the client device 102. The transformation system operating within the messaging client 104 determines the presence of a face within the image or video stream and provides modification icons associated with a computer animation model to transform image data, or the computer animation model can be present as associated with an interface described herein. The modification icons include changes that may be the basis for modifying the user's face within the image or video stream as part of the modification operation. Once a modification icon is selected, the transform system initiates a process to convert the image of the user to reflect the selected modification icon (e.g., generate a smiling face on the user). A modified image or video stream may be presented in a graphical user interface displayed on the client device 102 as soon as the image or video stream is captured, and a specified modification is selected. The transformation system may implement a complex convolutional neural network on a portion of the image or video stream to generate and apply the selected modification. That is, the user may capture the image or video stream and be presented with a modified result in real-time or near real-time once a modification icon has been selected. Further, the modification may be persistent while the video stream is being captured, and the selected modification icon remains toggled. Machine taught neural networks may be used to enable such modifications.

The graphical user interface, presenting the modification performed by the transform system, may supply the user with additional interaction options. Such options may be based on the interface used to initiate the content capture and selection of a particular computer animation model (e.g., initiation from a content creator user interface). In various embodiments, a modification may be persistent after an initial selection of a modification icon. The user may toggle the modification on or off by tapping or otherwise selecting the face being modified by the transformation system and store it for later viewing or browse to other areas of the imaging application. Where multiple faces are modified by the transformation system, the user may toggle the modification on or off globally by tapping or selecting a single face modified and displayed within a graphical user interface. In some embodiments, individual faces, among a group of multiple faces, may be individually modified, or such modifications may be individually toggled by tapping or selecting the individual face or a series of individual faces displayed within the graphical user interface.

A story table 312 stores data regarding collections of messages and associated image, video, or audio data, which are compiled into a. collection (e.g., a story or a gallery). The creation of a particular collection may be initiated by a particular user (e.g., each user for which a record is maintained in the entity table 304). A user may create a "personal story" in the form of a collection of content that has been created and sent/broadcast by that user. To this end, the user interface of the messaging client 104 may include an icon that is user-selectable to enable a sending user to add specific content to his or her personal story.

A collection may also constitute a "live story," which is a collection of content from multiple users that is created manually, automatically, or using a. combination of manual and automatic techniques. For example, a "live story" may constitute a curated stream of user-submitted content from various locations and events. Users whose client devices have location services enabled and are at a common location event at a particular time may, for example, be presented with an option, via a user interface of the messaging client 104, to contribute content to a particular live story. The live story may be identified to the user by the messaging client 104, based on his or her location. The end result is a "live story" told from a community perspective.

A further type of content collection is known as a "location story," which enables a user whose client device 102 is located within a specific geographic location (e.g., on a college or university campus) to contribute to a particular collection. In some embodiments, a contribution to a location story may require a second degree of authentication to verify that the end user belongs to a specific organization or other entity (e.g., is a student on the university campus).

As mentioned above, the video table 314 stores video data that, in one example, is associated with messages for which records are maintained within the message table 302. Similarly, the image table 316 stores image data associated with messages for which message data is stored in the entity table 304. The entity table 304 may associate various augmentations from the augmentation table 310 with various images and videos stored in the image table 316 and the video table 314.

Data Communications Architecture

Figure 4:
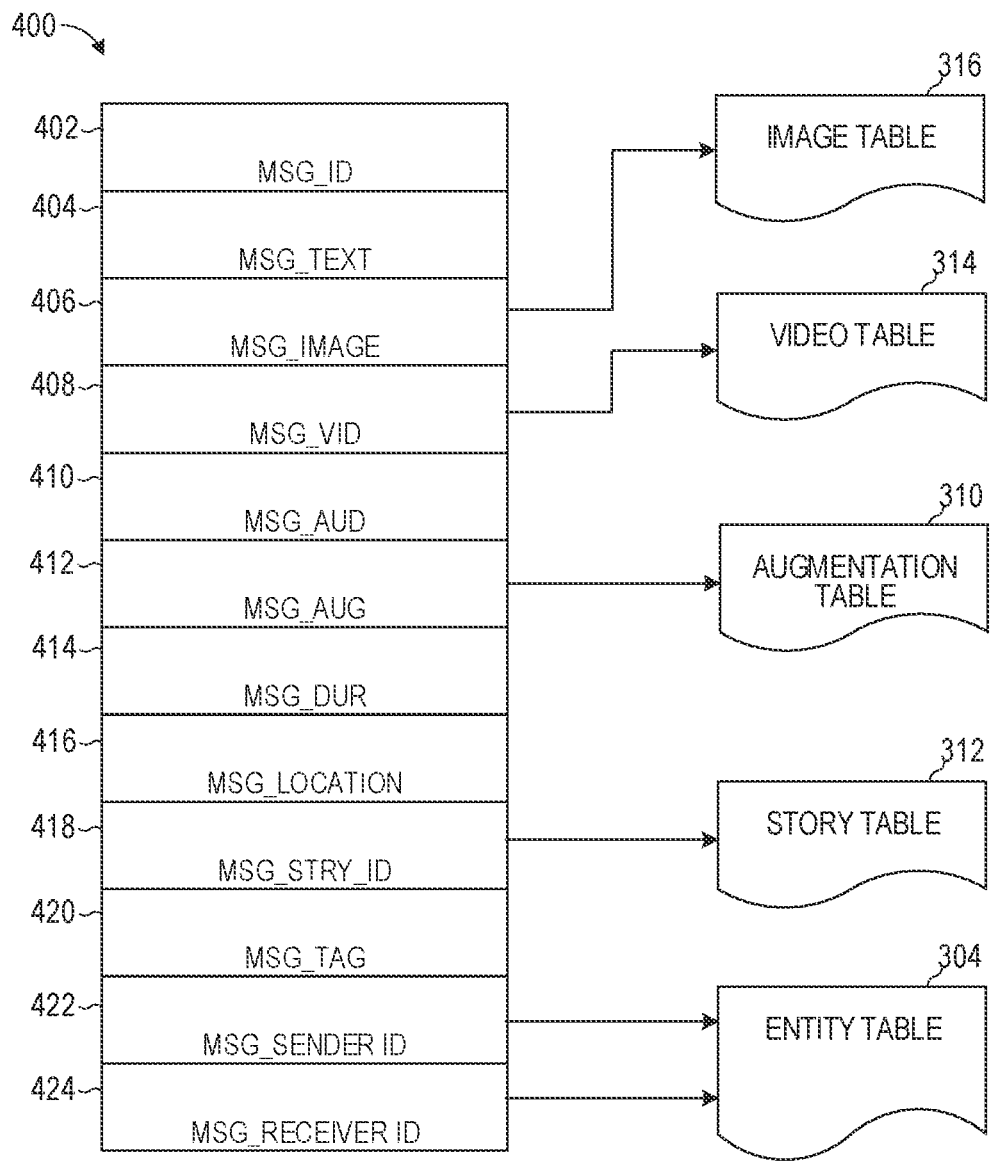
FIG. 4 is a schematic diagram illustrating a structure of a message generated by a messaging client for communication, according to example embodiments.

FIG. 4 is a schematic diagram illustrating a structure of a message 400, according to some examples, generated by a messaging client 104 for communication to a further messaging client 104 or the messaging server 114. The content of a particular message 400 is used to populate the message table 302 stored within the database 120, accessible by the messaging server 114. Similarly, the content of a message 400 is stored in memory as "in-transit" or "in-flight" data of the client device 102 or the application servers 112. A message 400 is shown to include the following example components:

message identifier 402: a unique identifier that identifies the message 400.

message text payload 404: text, to be generated by a user via a user interface of the client device 102, and that is included in the message 400.

message image payload 406: image data, captured by a camera component of a client device 102 or retrieved from a memory component of a client device 102, and that is included in the message 400. image data for a sent or received message 400 may be stored in the image table 316.

message video payload 408: video data, captured by a camera component or retrieved from a memory component of the client device 102, and that is included in the message 400. Video data for a sent or received message 400 may be stored in the video table 314.

message audio payload 410: audio data, captured by a microphone or retrieved from a memory component of the client device 102, and that is included in the message 400, message augmentation data 412: augmentation data (e.g., filters, stickers, or other annotations or enhancements) that represents augmentations to be applied to message image payload 406, message video payload 408, or message audio payload 410 of the message 400. Augmentation data for a sent or received message 400 may be stored in the augmentation table 310.

message duration parameter 414: parameter value indicating, in seconds, the amount of time for which content of the message (e.g., the message image payload 406, message video payload 408, message audio payload 410) is to be presented or made accessible to a user via the messaging client 104.

message geolocation parameter 416: geolocation data (e.g., latitudinal and longitudinal coordinates) associated with the content payload of the message. Multiple message geolocation parameter 416 values may be included in the payload, each of these parameter values being associated with respect to content items included in the content (e.g., a specific image within the message image payload 406, or a specific video in the message video payload 408).

message story identifier 418: identifier values identifying one or more content collections (e.g., "stories" identified in the story table 312) with which a particular content item in the message image payload 406 of the message 400 is associated. For example, multiple images within the message image payload 406 may each be associated with multiple content collections using identifier values.

message tag 420: each message 400 may be tagged with multiple tags, each of which is indicative of the subject matter of content included in the message payload. For example, where a particular image included in the message image payload 406 depicts an animal (e.g., a lion), a tag value may be included within the message tag 420 that is indicative of the relevant animal. Tag values may be generated manually, based on user input, or may be automatically generated using, for example, image recognition.

message sender identifier 422: an identifier (e.g., a messaging system identifier, email address, or device identifier) indicative of a user of the client device 102 on which the message 400 was generated and from which the message 400 was sent.

message receiver identifier 424: an identifier (e.g., a messaging system identifier, email address, or device identifier) indicative of a user of the client device 102 to which the message 400 is addressed.

The contents (e.g., values) of the various components of message 400 may be pointers to locations in tables within which content data values are stored. For example, an image value in the message image payload 406 may be a pointer to (or address of) a location within an image table 316. Similarly, values within the message video payload 408 may point to data stored within a video table 314, values stored within the message augmentation data 412 may point to data stored in an augmentation table 310, values stored within the message story identifier 418 may point to data stored in a story table 312, and values stored within the message sender identifier 422 and the message receiver identifier 424 may point to user records stored within an entity table 304.

Figure 5A:
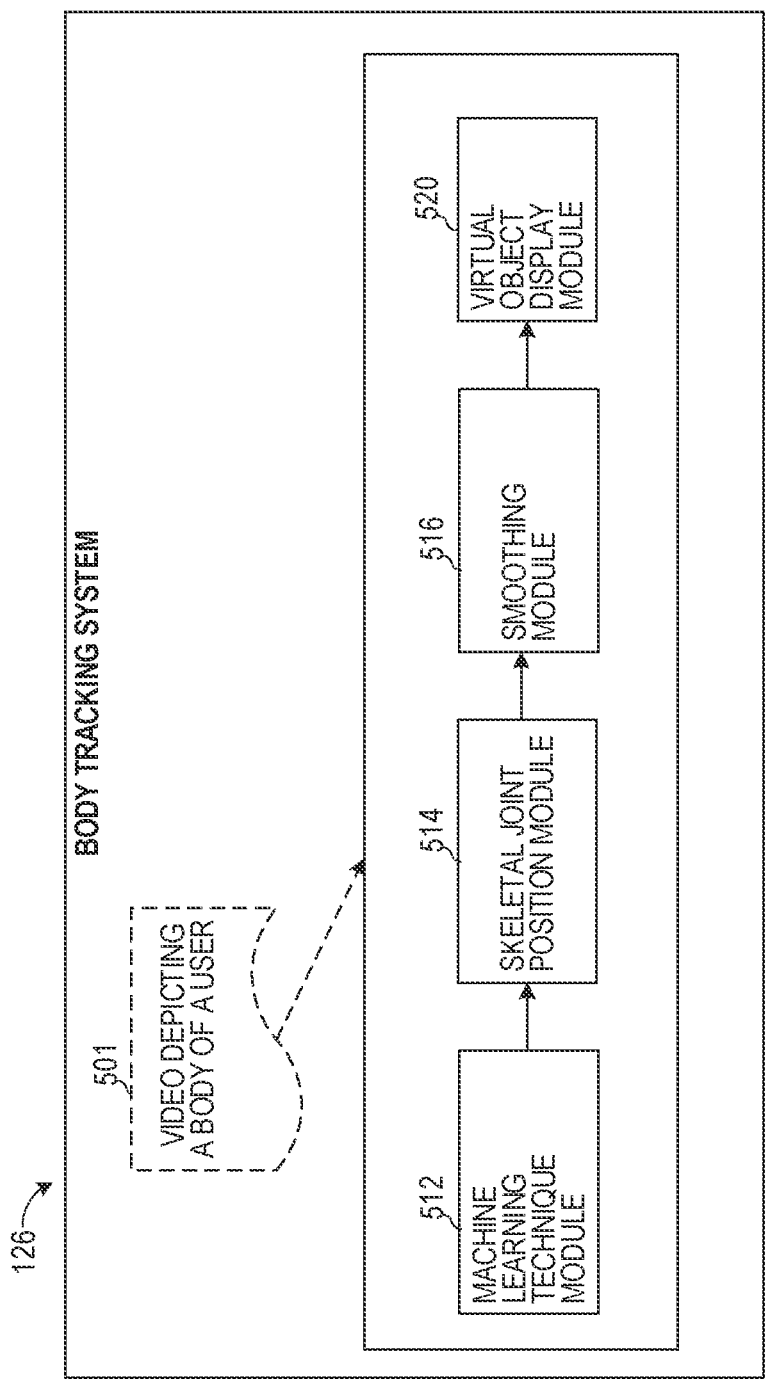
FIG. 5A is a block diagram showing an example body tracking system, according to example embodiments.

FIG. 5A is a block diagram showing an example body tracking system 126, according to example embodiments. Body tracking system 126 operates on a set of input data (e.g., a video 501 depicting a real-world body of a user). Body tracking system 126 includes a machine learning technique module 512, a skeletal joint position module 514, a smoothing module 516, and a virtual object display module 520.

In some embodiments, the body tracking system 126 includes a user detection component (not shown). The user detection component is activated in response to receiving input from the user that activates the front or rear facing camera of a client device 102. Once activated, the user detection component analyzes features of a set of images captured by the camera of the client device. The user detection component determines whether the features match an object that corresponds to a human or person. In such cases, the user detection component initiates the process for tracking the movement of the user across frames of a video (e.g., the set of images). Specifically, the user detection component instructs the machine learning technique module 512, skeletal joint position module 514 and the smoothing module 516 to track the skeletal joints of the user and smooth the movement of the one set of joints independently or smoothing movement of another set of joints across the frames of the video. In some cases, the user detection component is part of the machine learning technique module 512.

The machine learning technique module 512 (e.g., a deep neural network) extracts one or more features from the given input video to estimate skeletal joint positions of the skeletal joints depicted in the video. For example, the machine learning technique module 512 obtains the given video depicting a user's face, arms, torso, hips and legs. The machine learning technique module 512 extracts features from the video that correspond to the user's face and arms to identify one or more skeletal joints (e.g., the joints shown in FIG. 6 including the left/right wrist joints, left/right elbow joints, left/right shoulder joints, and a nose position).

The machine learning technique module 512 generates pairs of joints or sets of joints that are to be smoothed. For example, the machine learning technique module 512 communicates with the skeletal joint position module 514 to assign different sets of joints to be tracked and smoothed independently of other sets of joints. As an example, the skeletal joint position module 514 may assign the neck joint and shoulder joint as a first pair of joints to be tracked and smoothed together; may assign the hip joint, the left leg joint and the left knee joint as another set of joints to be tracked and smoothed together, and so forth. Any number of joints (e.g., one joint, two joints, three joints that are adjacent) less than all of the joints that are detected can be included in a given set of joints that are tracked and smoothed collectively. In this way, the skeletal joint position module 514 tracks the joints that are part of one set separately from the joints that are part of another set to measure noise across the set of video frames and to adjust smoothing being applied to one set independently of smoothing applied to another set of the joints.

The extracted features of the machine learning technique module 512 are provided to the skeletal joint position module 514, The skeletal joint position module 514 analyzes the skeletal joint features to determine coordinates of specific skeletal joints. For example, the skeletal joint position module 514 determines the x,y coordinates of a particular point of each skeletal joint, such as the x,y coordinates of the left wrist, the x,y coordinates of the left elbow, the x,y coordinates of the left shoulder, the x,y coordinates of the nose (or other facial feature such as mouth, ears or eyes), the x,y coordinates of the right wrist, the x,y coordinates of the right elbow, and the x,y coordinates of the right shoulder. Using these coordinates, the skeletal joint position module 514 assigns pairs or sets of joints.

In some cases, a neural network or machine learning technique can be applied to adaptively and automatically select those joints to be tracked and smoothed that are part of each set. For example, the machine learning technique may be trained based on a set of training videos to predict that a first set of joints (e.g., the neck joint, left shoulder joint, and left elbow joint) move more or results in a greater amount of noise across a set of frames than another set of joints (e.g., the hip joint and the left leg joint). In this case, the machine learning technique may instruct the skeletal joint position module 514, when operating on a new set of video frames, to form a first set of joints that includes the neck joint, left shoulder joint, and left elbow joint and exclude from the first set the hip joint and the left leg joint. Alternatively, the skeletal joint position module 514 may only track and smooth those sets of joints that are predicted by the matching learning technique to have a greater than a threshold amount of noise from a set of training videos. In some other cases, the sets of joints that are tracked and smoothed are manually specified by a user.

The smoothing module 516 retrieves a set of smoothing filters 306 and applies the smoothing filters 306 to a first set of the joints provided by the skeletal joint position module 514 independently of applying the smoothing filters 306 to a second set of the joints provided by the skeletal joint position module 514. For example, the smoothing module 516 applies a first set of smoothing filters in parallel to the first set of the plurality of skeletal joints. The smoothing module 516 applies a second set of smoothing filters in parallel to the second set of the plurality of skeletal joints. The smoothing module 516 adapts a first parameter of the first set of smoothing filters independently of a second parameter of the second set of smoothing filters. For example, the smoothing module 516 adapts the weights of each of the filters in the first set of smoothing filters to control the amount of smoothing applied to the first set of joints. The smoothing module 516 aggregates the weighted output of the filters that are applied to the first set of joints.

In some embodiments, the smoothing module 516 accesses a set of previous frames (e.g., 1-2 seconds of past video). The smoothing module 516 analyzes movement of the skeletal joints or sets of the skeletal joints across the set of previous frames. The smoothing module 516 applies a plurality of smoothing filters to the first set of skeletal joints that appear in the previous frames, such as after or before measuring a signal quality parameter representing an amount of noise in movement of the skeletal joints. The smoothing module 516 also applies to the second set of skeletal joints the same or a different plurality of smoothing filters with the same or different smoothing parameters as the smoothing filters applied to the first set of skeletal joints. In some implementations, the plurality of smoothing filters are applied in parallel to the first set of skeletal joints and the plurality of smoothing filters are also applied in parallel to the second set of skeletal joints. Namely, first and second smoothing filters of the plurality of smoothing filters are applied concurrently or in parallel to smooth movement of the first set of skeletal joints across the set of previous frames. As another example, second and third smoothing filters of the plurality of smoothing filters are applied concurrently or in parallel to smooth movement of the second set of skeletal joints across the set of previous frames. The outputs of the smoothing filters applied to the first/second set of skeletal joints are weighted and summed based on the signal quality parameter.

The smoothing module 516 measures signal stability using a signal stability parameter for each of the first and second sets of skeletal joints. Specifically, the smoothing module 516 measures an amount of noise resulting from smoothing the first set of skeletal joints across the previous frames and separately measures the amount of noise resulting from smoothing the second set of skeletal joints across the previous frames. Based on the amount of noise resulting from the smoothing operations, the smoothing module 516 adjusts the smoothing parameters of the smoothing filters applied to the different sets of skeletal joints and to the same sets of skeletal joints (e.g., by controlling the amount of weights applied to each of multiple filters that are applied to the same set of skeletal joints). The smoothing module 516, in some implementations, interpolates outputs of the smoothing and movement of the first skeletal joints to measure the noise and separately interpolates outputs of the smoothing and movement of the second skeletal joints to measure the noise in movement of the different sets of joints.

In one example, the smoothing module 516 determines that the interpolated movement of the first set of skeletal joints results in noise that exceeds a threshold value. Namely, the signal stability parameter measured and computed that represents the noise in the movement of the first set of skeletal joints may exceed the threshold value. In such circumstances, the amount of noise may be indicative of the need for additional smoothing. As such, the smoothing module 516 increases the smoothing parameter of the plurality of smoothing filters (or a subset of the smoothing filters) that are applied to the first set of skeletal joints when a subsequent set of video frames are received and processed or for the current set of frames in which the noise was measured. Namely, the smoothing module 516 can measure noise in a set of frames and then adjust the amount of smoothing applied to the joints of the person depicted in the set of frames based on the measured noise. As an example, the smoothing module 516 controls the weights of the smoothing filters applied in parallel to a given set of joints based on the signal stability parameter. One smoothing filter with one characteristics can be weighted more heavily than a second smoothing filter with another characteristic applied in parallel to the same set of joints.

In another example, the smoothing module 516 determines that the interpolated movement of the second set of skeletal joints results in noise that fails to exceed (or is less than) a threshold value. Tamely, the signal stability parameter measured and computed that represents the noise in the movement of the second set of skeletal joints may fail to exceed the threshold value. In such circumstances, the amount of noise may be indicative of the need for less smoothing. As such, the smoothing module 516 decreases the smoothing parameter of the plurality of smoothing filters (or a subset of the smoothing filters) that are applied to the second set of skeletal joints when a subsequent set of video frames is received and processed or for the current set of frames in which the noise was measured. In one implementation, different smoothing may be applied to the first set of skeletal joints than that which is applied at the same time to the second set of skeletal joints.

In some cases, the threshold value against which noise resulting from movement of the first set of skeletal joints may differ from the threshold value against which noise resulting from movement of the second set of skeletal joints. In some cases, the two threshold values may be the same. Namely, each set of skeletal joints may be associated with a different threshold value against which their respective signal stability parameter is compared to adjust the smoothing parameter.

Figure 5B:
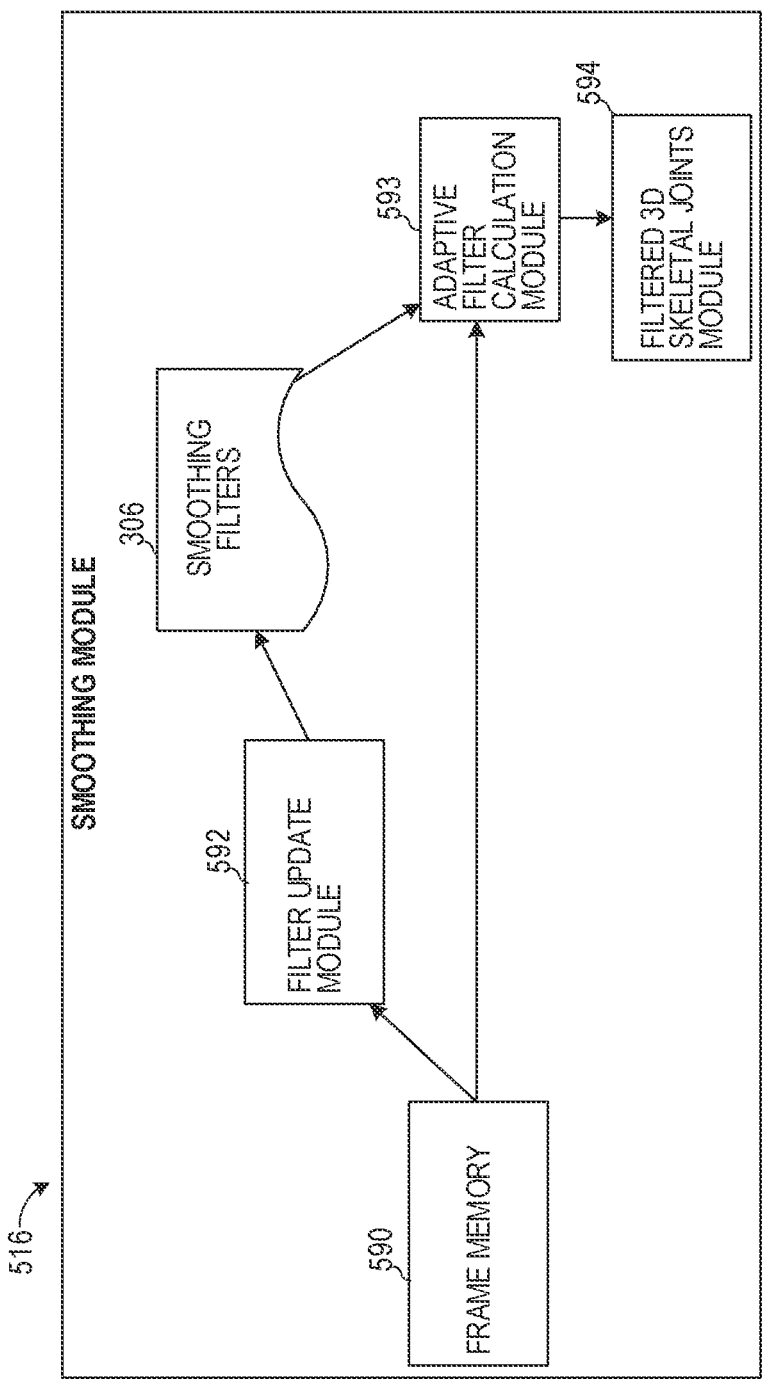
FIG. 5B is a block diagram showing an example smoothing module, according to example embodiments.

FIG. 5B is a block diagram showing an example smoothing module 516, according to example embodiments. The smoothing module 516 includes or accesses a frame memory 590, a filter update module 592, smoothing filters 306, an adaptive filter calculation module 593 and a filtered 3D skeletal joints module 594.

The frame memory 590 includes a window of previous frames of the received real-time video 501 and the keypoints and scores of those frames. The number of previous frames can include any number of frames (e.g., 2 frames, 10 frames, 100 frames, or any other suitable number). The smoothing module 516 initializes a set of K motion filters by accessing the smoothing filters 306. The number K in the set of motion filters can be selected based on the number of joints to be tracked and smoothed or the number of sets of joints to be tracked and smoothed. For example, if there are three sets of joints to be tracked and smoothed, then three different motion filters can be selected to be configured using different respective characteristics.

In some embodiments, each motion filter of the set of K motion filters includes X different versions. As an example, the motion filter can include soft and aggressive characteristics, where when the motion filter is configured with the soft characteristic, the responsiveness of the motion filter can be increased than when configured with the aggressive characteristic. The amount of smoothing (e.g., the value of a weight applied to the smoothing filter outputs) is controlled so as to increase responsiveness of the smoothing filters without oversmoothing or undersmoothing. Namely, when there is noise in movement of the joints in a given window of frames that exceeds a threshold value, the output of an aggressive filter is weighted more heavily than the output of a soft filter applied to the same set of joints which reduces responsiveness but increases smoothing. When there is noise in movement of the joints in a given window of frames that is less than a threshold value, the output of an aggressive filter is weighted less heavily than the output of a soft filter applied to the same set of joints which increases responsiveness but reduces smoothing. Initially, the filter update module 592 communicates with the smoothing filters 306 to obtain the set of K motion filters and an initial set of characteristics of each obtained filter.

After the number of frames in the frame memory 590 are processed to evaluate the signal quality parameter S, the filter update module 592 adjusts or selects the characteristics of each of the obtained filters. The smoothing module 516 can compute the signal quality parameter S as a function of a standard deviation of differences between adjacent frames in the set of frames. Specifically, the smoothing module 516 computes the signal quality parameter S in accordance with: $s_t = std_t(\{d_i | t-T \ldots t\})$, where T is the number of frames in the set of frames in the frame memory 590, and $d_i = x_i x_{i-1}$ is a difference between two adjacent frames.

In some implementations, a first filter that is selected to be applied to a first set of joints can be configured to have a soft characteristic if the signal quality parameter S associated with the first set of joints is greater than a specified threshold. As another example, a second filter that is selected to be applied to the first set of joints can be configured to have an aggressive characteristic if the signal quality parameter S associated with the first set of joints is less than a specified threshold. In some cases, the outputs of the filters are specified and controlled by weights. Namely, a weight applied to an aggressive filter with a higher value than the weight applied to the soft filter can result in a greater amount of smoothing being applied to the set of skeletal joints but decreased responsiveness. weight applied to an aggressive filter with a lower value than the weight applied to the soft filter can result in a softer amount of smoothing being applied to the set of skeletal joints with increased responsiveness.

In some embodiments, the filter update module 592 weighs between soft and aggressive filters applied to a given set of joints in parallel based on a measure of the number of stable frames with the signal quality parameter S being below a predefined threshold. This value is averaged in the window of frames in the frame memory 590 based on the weight associated with the respective filter. Specifically, the filter update module 592 computes a first weight associated with a soft filter characteristic as a function of $w_{soft} = E[s_t < Thres]$ and computes a second weight associated with an aggressive filter characteristic as a function of $w_{agressive} E[s_t \geq Thres]$. In this way, if the signal quality parameter S (e.g., the standard deviation measure of the stability for the past number of frames) is below the threshold, the soft weight ($w_{soft}$) is selected to be applied by the motion filter to the corresponding set of joints. If the signal quality parameter S (e.g., the standard deviation measure of the stability for the past number of frames) is above or equal to the threshold, the aggressive weight ($w_{aggressive}$) is selected to be applied by the motion filter to the corresponding set of joints. As an example, if the signal quality parameter S (e.g., the standard deviation measure of the stability for the past number of frames) is above or equal to the threshold, the weight of the output of the aggressive filter is increased relative to the weight of the output applied to a softer filter to aggregate smoothing of the motion of the skeletal joints.

Multiple filters can be applied to the same set of joints in parallel. Each of the multiple filters can include a different filter characteristic. For example, a. soft motion filter can be applied to a first set of joints in parallel with an aggressive motion filter. The filter update module 592 may assign a lower weight to the output of the soft motion filter than the weight assigned to the output of the aggressive motion filter if the signal quality parameter S (e.g., the standard deviation measure of the stability for the past number of frames) is above or equal to the threshold. As another example, the filter update module 592 may assign a greater weight to the output of the soft motion filter than the weight assigned to the output of the aggressive motion filter if the signal quality parameter S (e.g., the standard deviation measure of the stability for the past number of frames) is below the threshold.. The smoothed motion of the 3D skeletal joints corresponding to the set of joints can then be based on the weighted combination of the soft and aggressive motion filters.

The adaptive filter calculation module 593 aggregates the set of filters with the respective weights. In some embodiments, the adaptive filter calculation module 593 retrieves the set of frames from the frame memory 590 and applies the filters with the associated weights to the corresponding skeletal joint sets using the filtered 3D skeletal joints module 594. Specifically, the adaptive filter calculation module 593 receives the raw 3D skeletal joints from the skeletal joint position module 514 and filters the movement of the 3D skeletal joints across the set of frames in the frame memory 590 (or frames received in a subsequent window of frames) using the aggregated set of filters. For example, the adaptive filter calculation module 593 computes the final signal in accordance with:

$$\overline{x} = \sum_i^X w f_i(x),$$

where $f_i(x)$ represents a motion filter i applied to a set of joints x with a given weight $w_i$, for all filters X. In this way, each filter applied to the same set of joints can be assigned a different weight and the outputs of all the filters applied to the same set of joints is aggregated to smooth motion of the joints.

The filtered 3D skeletal joints are output as an average of the weighted filter outputs $f_i(x)$ applied to the joints that appear in each respective frame that is in the frame memory 590. Specifically, the adaptive filter calculation module 593 obtains a first frame from the frame memory 590 and identifies a set of joints of a person depicted in the first frame. The adaptive filter calculation module 593 smooths movement of the set of joints from the first frame to a next adjacent frame or through the set of frames according to the motion filter with the selected filter characteristic (e.g., aggressive or soft filter or weighted combination of the aggressive and soft filters) for that set of joints. In some cases, the adaptive filter calculation module 593 applies a soft filter to the set of joints that appear in a first collection of frames in the set of frames in the frame memory 590 and then switches to applying an aggressive filter to the same set of joints that appear in a second collection of frames in the set of frames in the frame memory 590. This may be the result in the case that the second collection of frames has a lower signal quality parameter for the set of joints than the first collection of frames. In some cases, where the signal quality parameter for a set of frames is below a threshold value, the adaptive filter calculation module 593 applies weight with a first value to a soft filter to smooth a set of joints that appear in a first collection of frames in the set of frames in the frame memory 590 and applies a weight with a greater second value to an aggressive filter to smooth the same set of joints that appear in the first collection of frames. This results in a greater amount of smoothing being applied to the set of joints in the first collection of frames.

In this way, the smoothing module 516 operates on a set of previously received frames of a video to compute a signal quality parameter representing noise in movement of a set of joints or multiple sets of joints of an object or person depicted in the set of frames. Based on the signal quality, the smoothing module 516 selectively and adaptively modifies the quantity of smoothing (e.g., how strong or weak a motion filter characteristic is set) applied respective joints in the sets of joints. Then, the respective joints in the previously received frames are smoothed using the respective filters with the same or different motion filter characteristics. After or during smoothing the movement of the joints in the previously received frames, an avatar or virtual object can be adaptively moved in a similar smoothed manner according to the smoothed movement of the joints of the real-world object or person.

The virtual object display module 520 can adjust a skeletal rig of a given avatar based on the smoothed skeletal joints detected and tracked from the video of the user. The virtual object display module 520 adjusts the way in which the avatar is moved in an image, such as by changing the pose, a visual attribute and/or a position of the avatar in the image. In some embodiments, the virtual object display module 520 combines the adjusted avatar into the received video depicting the user's body so that both the adjusted avatar and the user are simultaneously presented in a video. The image is provided by the virtual object display module 520 to the client device 102 and can then be sent to another user or stored for later access and display.

Figure 7:
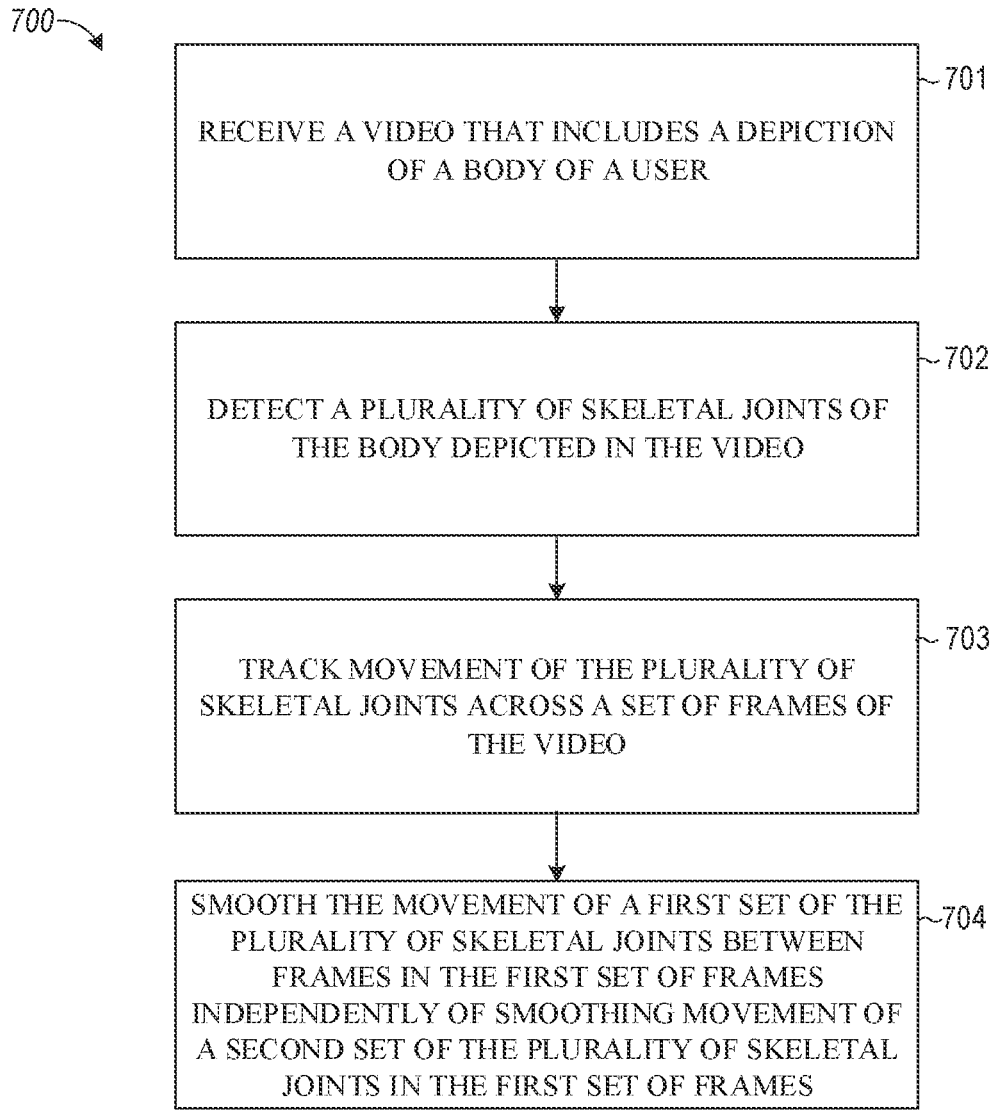
FIG. 7 is a flowchart illustrating example operations of the body tracking system, according to example embodiments.

FIG. 7 is a flowchart illustrating example operations of the body tracking system 126 in performing process 700, according to example embodiments. The process 700 may be embodied in computer-readable instructions for execution by one or more processors such that the operations of the process 700 may be performed in part or in whole by the functional components of the messaging server system 108 and/or AR/VR application 105; accordingly, the process 700 is described below by way of example with reference thereto. However, in other embodiments, at least some of the operations of the process 700 may be deployed on various other hardware configurations. The process 700 is therefore not intended to be limited to the messaging server system 108 and can be implemented in whole, or in part, by any other component. Some or all of the operations of process 700 can be in parallel, out of order, or entirely omitted.

At operation 701, the body tracking system 126 receives a video that includes a depiction of a body of a user. For example, the machine learning technique module 512 receives the video 501 depicting a body of a user. The machine learning technique module 512 extracts one or more features from the image indicating skeletal joints.

Figure 6:
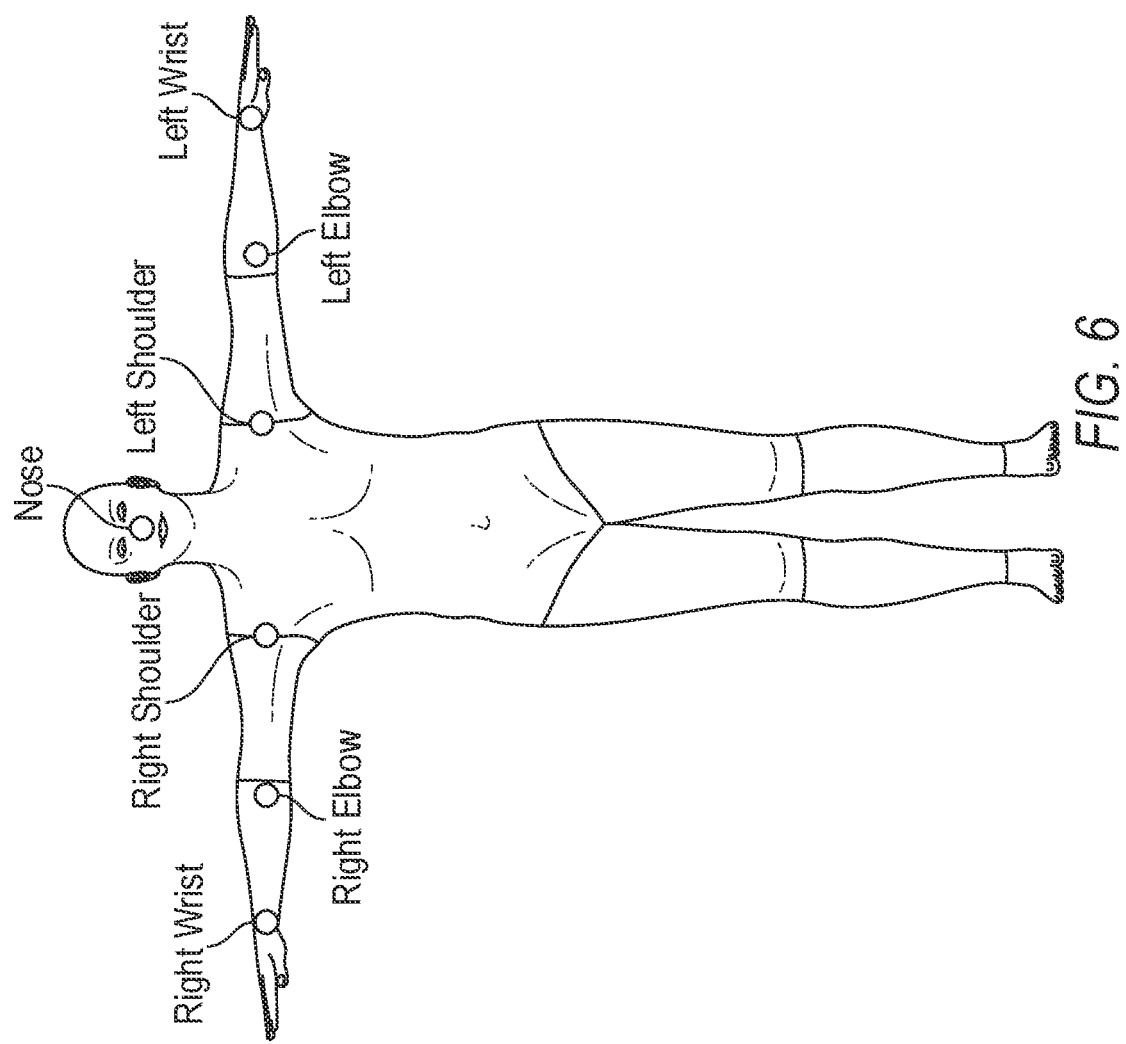
FIG. 6 is a diagram showing body joint positions used to track the body in a video, according to example embodiments.

At operation 702, the body tracking system 126 detects a plurality of skeletal joints of the body depicted in the video. For example, the skeletal joint position module 514 receives the output of the machine learning technique module 512 and marks or generates a depiction of the skeletal joints, as shown in FIG. 6 for tracking the joints across a set of frames.

At operation 703, the body tracking system 126 tracks movement of the plurality of skeletal joints across a set of frames of the video. For example, the skeletal joint position module 514 collects different sets or pairs of skeletal joints into different groups to be tracked and smoothed. In some cases, the skeletal joint position module 514 groups those joints that are determined from a machine learning technique to result in a greatest amount of noise in a same group as long as they are all adjoining joints.

At operation 704, the body tracking system 126 smooths the movement of a first set of the plurality of skeletal joints between frames in the first set of frames independently of smoothing movement of a second set of the plurality of skeletal joints in the first set of frames. For example, the smoothing module 516 applies a first set of smoothing filters with one set of smoothing parameters to a first set of skeletal joints (e.g., the neck and left shoulder joints) and applies a second set of smoothing filters with another set of smoothing parameters to a second set of skeletal joints the hip and right knee joints). The smoothing module 516 may also in parallel apply to the same set of joints or to a single joint a plurality of smoothing filters with different characteristics. The smoothing module 516 assigns weights to the plurality of smoothing filters on the basis of the signal quality parameter representing noise in movement of the joints to which the filters are applied. The smoothing module 516 then aggregates a weighted sum of the plurality of smoothing filters that are applied to the same joint or set of joints to adaptively smooth movement of the joint across the set of frames.

Although the described flowchart can show operations as a sequential process, many of the operations can be performed in parallel or concurrently. In addition, the order of the operations may be re-arranged. A process is terminated when its operations are completed. A process may correspond to a method, a procedure, an algorithm, etc. The operations of methods may be performed in whole or in part, may be performed in conjunction with some or all of the operations in other methods, and may be performed by any number of different systems, such as the systems described herein, or any portion thereof, such as a processor included in any of the systems.

Figure 8:
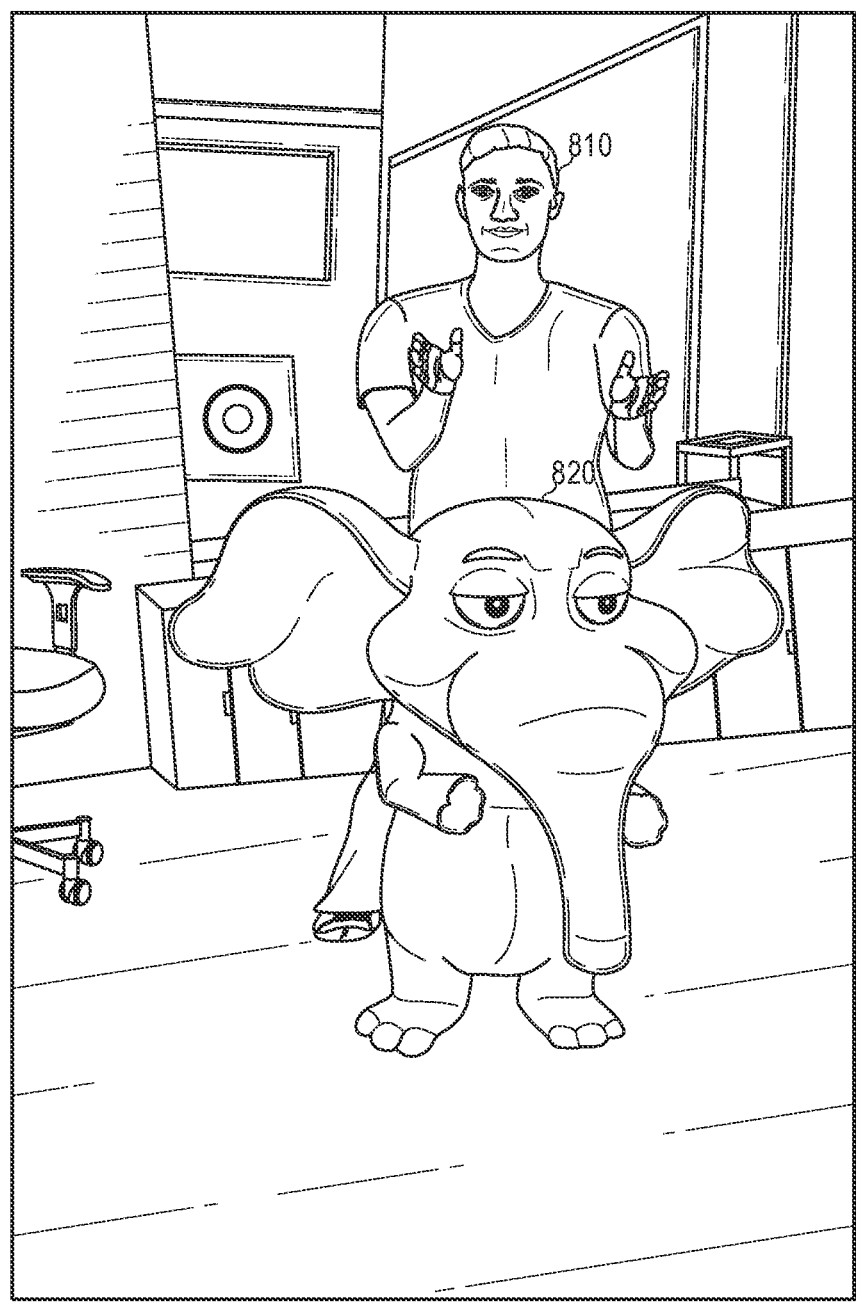
FIG. 8 shows illustrative inputs and outputs of the body tracking system, according to example embodiments.

FIG. 8 shows illustrative inputs and outputs of the body tracking system 126, according to example embodiments. As shown, an avatar is presented together with a person in a video. Movement of the person's skeletal joints is smoothed by the body tracking system 126. Consequently, the movement of the rig of the avatar is also smoothed resulting in the movement of the avatar presented on the display appearing more realistic and lifelike. Namely, the avatar is moved to mimic movement of the person in the video in a smoothed fashion. In some cases, the movement of one part of the avatar or one part of the skeletal rig of the avatar is smoothed independently and separately from movement of another part of the avatar. In some instances, the set of skeletal joints of the person that are smoothed match with the skeletal joints of the avatar that are smoothed. In this way, different parts or skeletal joints of the avatar can be smoothed separately using different smoothing filters or smoothing filters with different smoothing parameters.

Machine Architecture

Figure 9:
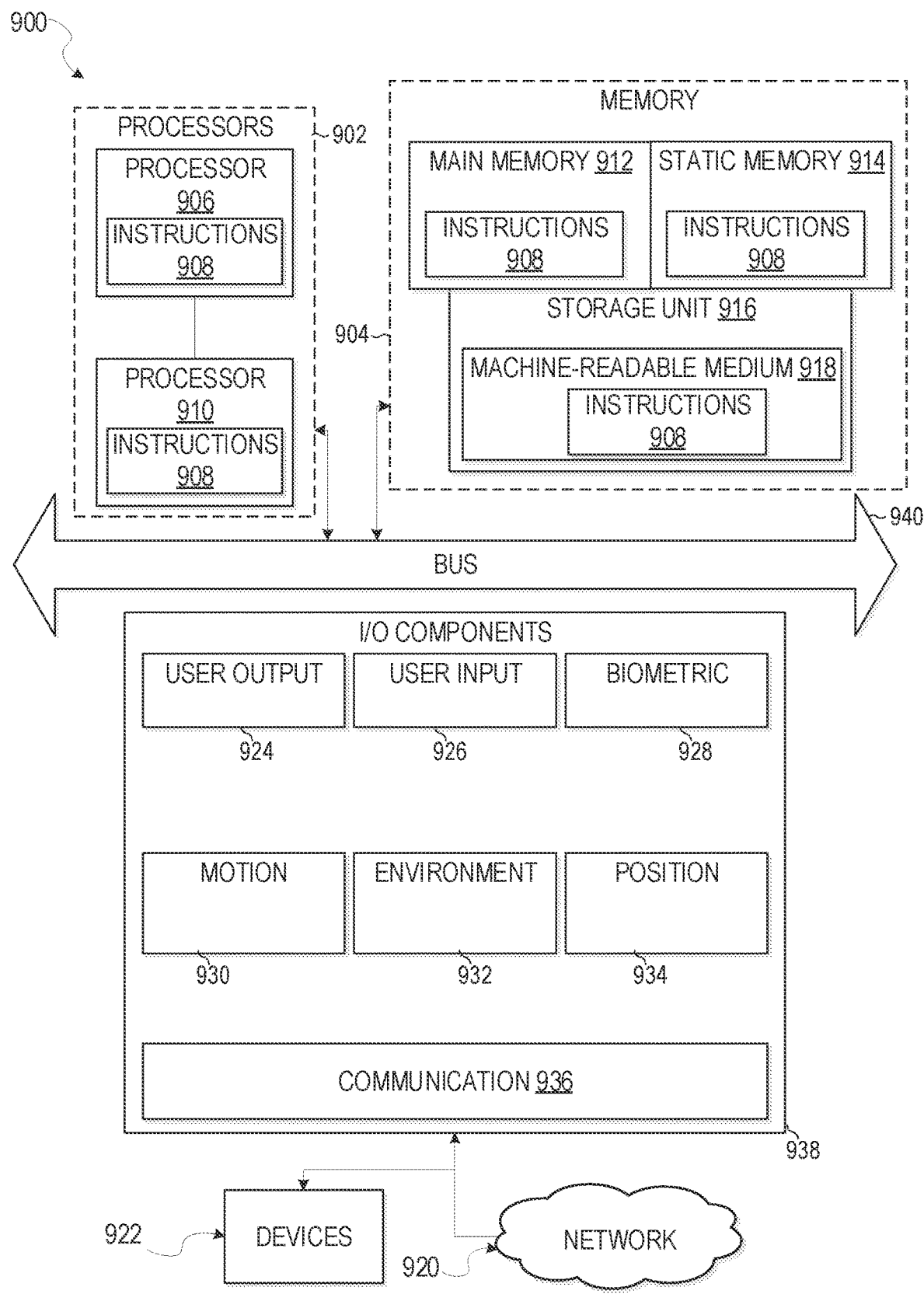
FIG. 9 is a diagrammatic representation of a machine in the form of a computer system within which a set of instructions may be executed for causing the machine to perform any one or more of the methodologies discussed herein, in accordance with some examples.

FIG. 9 is a diagrammatic representation of the machine 900 within which instructions 908 (e.g., software, a program, an application, an apples, an app, or other executable code) for causing the machine 900 to perform any one or more of the methodologies discussed herein may be executed. For example, the instructions 908 may cause the machine 900 to execute any one or more of the methods described herein. The instructions 908 transform the general, non-programmed machine 900 into a particular machine 900 programmed to carry out the described and illustrated functions in the manner described. The machine 900 may operate as a standalone device or may be coupled (e.g., networked) to other machines. In a networked deployment, the machine 900 may operate in the capacity of a server machine or a client machine in a server-client network environment, or as a peer machine in a peer-to-peer (or distributed) network environment. The machine 900 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smartphone, a mobile device, a wearable device (e.g., a smartwatch), a smart home device (e.g., a smart appliance), other smart devices, a web appliance, a network router, a network switch, a network bridge, or any machine capable of executing the instructions 908, sequentially or otherwise, that specify actions to be taken by the machine 900. Further, while only a single machine 900 is illustrated, the term "machine" shall also be taken to include a collection of machines that individually or jointly execute the instructions 908 to perform any one or more of the methodologies discussed herein. The machine 900, for example, may comprise the client device 102 or any one of a number of server devices forming part of the messaging server system 108. In some examples, the machine 900 may also comprise both client and server systems, with certain operations of a particular method or algorithm being performed on the server-side and with certain operations of the particular method or algorithm being performed on the client-side.

The machine 900 may include processors 902, memory 904, and input/output I/O components 938, which may be configured to communicate with each other via a bus 940. In an example, the processors 902 (e.g., a Central Processing Unit (CPU), a Reduced Instruction Set Computing (RISC) Processor, a Complex Instruction Set Computing (CISC) Processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, a processor 906 and a processor 910 that execute the instructions 908. The term "processor" is intended to include multi-core processors that may comprise two or more independent processors (sometimes referred to as "cores") that may execute instructions contemporaneously. Although FIG. 9 shows multiple processors 902, the machine 900 may include a single processor with a single-core, a single processor with multiple cores (e.g., a multi-core processor), multiple processors with a single core, multiple processors with multiples cores, or any combination thereof.

The memory 904 includes a main memory 912, a static memory 914, and a storage unit 916, both accessible to the processors 902 via the bus 940. The main memory 912, the static memory 914, and storage unit 916 store the instructions 908 embodying any one or more of the methodologies or functions described herein. The instructions 908 may also reside, completely or partially, within the main memory 912, within the static memory 914, within machine-readable medium 918 within the storage unit 916, within at least one of the processors 902 (e.g., within the Processor's cache memory), or any suitable combination thereof, during execution thereof by the machine 900.

The I/O components 938 may include a wide variety of components to receive input, provide output, produce output, transmit information, exchange information, capture measurements, and so on. The specific I/O components 938 that are included in a particular machine will depend on the type of machine. For example, portable machines such as mobile phones may include a touch input device or other such input mechanisms, while a headless server machine will likely not include such a touch input device. It will be appreciated that the I/O components 938 may include many other components that are not shown in FIG. 9. In various examples, the I/O components 938 may include user output components 924 and user input components 926. The user output components 924 may include visual components (e.g., a display such as a plasma display panel (PDP), a light-emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The user input components 926 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and force of touches or touch gestures, or other tactile input components), audio input components (e.g., a microphone), and the like.

In further examples, the I/O components 938 may include biometric components 928, motion components 930, environmental components 932, or position components 934, among a wide array of other components. For example, the biometric components 928 include components to detect expressions (e.g., hand expressions, facial expressions, vocal expressions, body gestures, or eye-tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 930 include acceleration sensor components (e.g., accelerometer), gravitation sensor components, rotation sensor components (e.g., gyroscope).

The environmental components 932 include, for example, one or cameras (with still image/photograph and video capabilities), illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment.

With respect to cameras, the client device 102 may have a camera system comprising, for example, front cameras on a front surface of the client device 102 and rear cameras on a rear surface of the client device 102. The front cameras may, for example, be used to capture still images and video of a user of the client device 102 (e.g., "selfies"), which may then be augmented with augmentation data (e.g., filters) described above. The rear cameras may, for example, be used to capture still images and videos in a more traditional camera mode, with these images similarly being augmented with augmentation data. In addition to front and rear cameras, the client device 102 may also include a 360° camera for capturing 360° photographs and videos.

Further, the camera system of a client device 102 may include dual rear cameras (e.g., a primary camera as well as a depth-sensing camera), or even triple, quad or penta rear camera configurations on the front and rear sides of the client device 102. These multiple cameras systems may include a wide camera, an ultra-wide camera, a telephoto camera, a macro camera and a depth sensor, for example.

The position components 934 include location sensor components (e.g., a (IPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 938 further include communication components 936 operable to couple the machine 900 to a network 920 or devices 922 via respective coupling or connections. For example, the communication components 936 may include a network interface Component or another suitable device to interface with the network 920. In further examples, the communication components 936 may include wired communication components, wireless communication components, cellular communication components, Near Field Communication (NFC) components, Bluetooth®) components (e.g., Bluetooth Low Energy), Wi-Fi® components, and other communication components to provide communication via other modalities. The devices 922 may be another machine or any of a wide variety of peripheral devices (e.g., a peripheral device coupled via a USB).

Moreover, the communication components 936 may detect identifiers or include components operable to detect identifiers. For example, the communication components 936 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 936, such as location via Internet Protocol (IP) geolocation, location via Wi-Fi® signal triangulation, location via detecting an NFC beacon signal that may indicate a particular location, and so forth.

The various memories (e.g., main memory 912, static memory 914, and memory of the processors 902) and storage unit 916 may store one or more sets of instructions and data structures (e.g., software) embodying or used by any one or more of the methodologies or functions described herein. These instructions (e.g., the instructions 908), when executed by processors 902, cause various operations to implement the disclosed examples.

The instructions 908 may be transmitted or received over the network 920, using a transmission medium, via a network interface device a network interface component included in the communication components 936) and using any one of several well-known transfer protocols (e.g., hypertext transfer protocol (HTTP)). Similarly, the instructions 908 may be transmitted or received using a transmission medium via a coupling (e.g., a peer-to-peer coupling) to the devices 922.

Software Architecture

Figure 10:
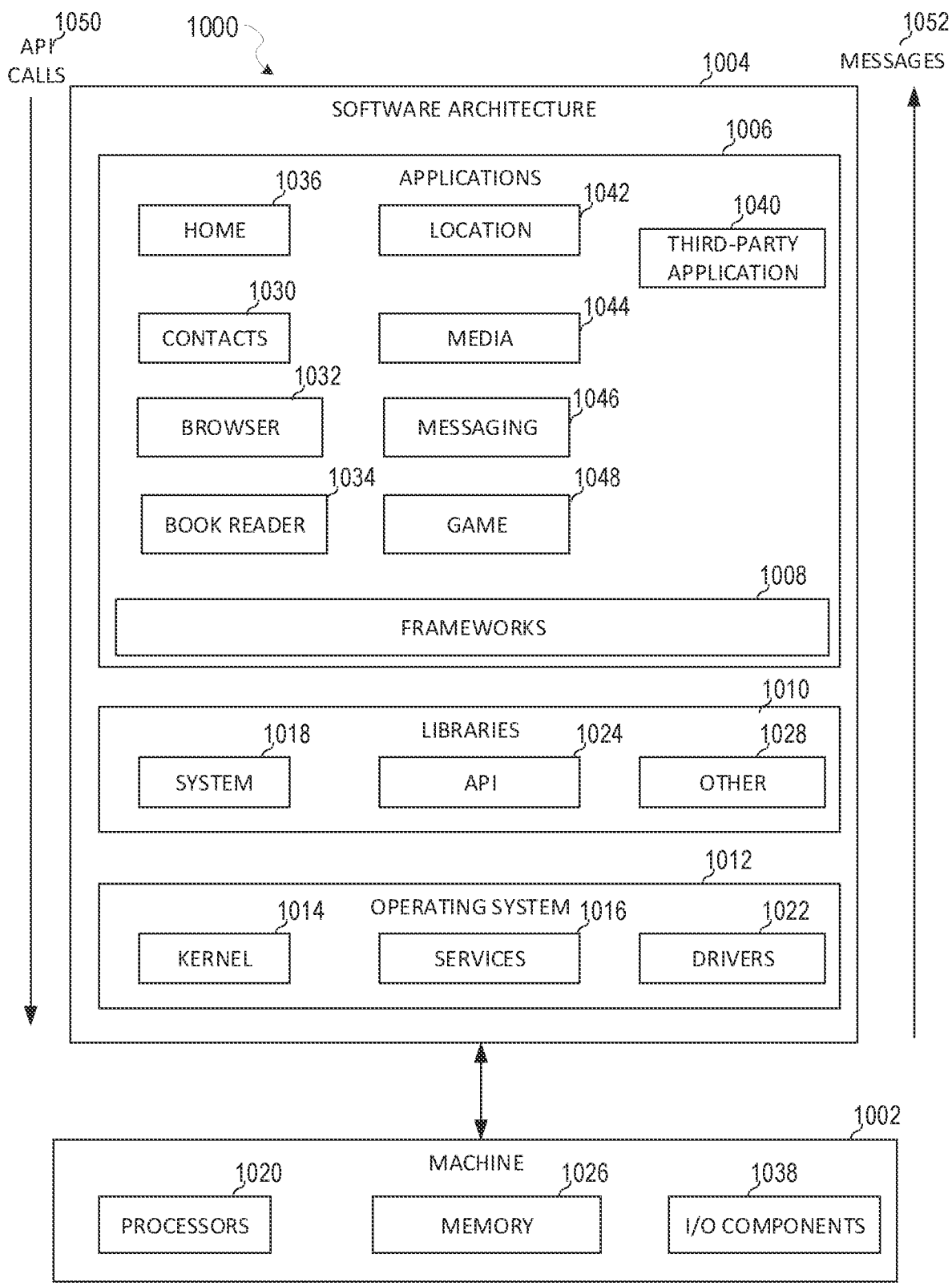
FIG. 10 is a block diagram showing a software architecture within which examples may be implemented.

FIG. 10 is a block diagram 1000 illustrating a software architecture 1004, which can be installed on any one or more of the devices described herein. The software architecture 1004 is supported by hardware such as a machine 1002 that includes processors 1020. memory 1026, and I/O components 1038. In this example, the software architecture 1004 can be conceptualized as a stack of layers, where each layer provides a particular functionality. The software architecture 1004 includes layers such as an operating system 1012, libraries 1010, frameworks 1008, and applications 1006. Operationally, the applications 1006 invoke API calls 1050 through the software stack and receive messages 1052 in response to the API calls 1050.

The operating system 1012 manages hardware resources and provides common services. The operating system 1012 includes, for example, a kernel 1014, services 1016, and drivers 1022. The kernel 1014 acts as an abstraction layer between the hardware and the other software layers. For example, the kernel 1014 provides memory management, processor management (e.g., scheduling), component management, networking, and security settings, among other functionality. The services 1016 can provide other common services for the other software layers. The drivers 1022 are responsible for controlling or interfacing with the underlying hardware. For instance, the drivers 1022 can include display drivers, camera drivers, BLUETOOTH® or BLUETOOTH® Low Energy drivers, flash memory drivers, serial communication drivers (e.g., USB drivers), WI-FI® drivers, audio drivers, power management drivers, and so forth.

The libraries 1010 provide a common low-level infrastructure used by the applications 1006. The libraries 1010 can include system libraries 1018 (e.g., C standard library) that provide functions such as memory allocation functions, string manipulation functions, mathematic functions, and the like. In addition, the libraries 1010 can include API libraries 1024 such as media libraries (e.g., libraries to support presentation and manipulation of various media formats such as Moving Picture Experts Group-4 (MPEG4), Advanced Video Coding (H.264 or AVC), Moving Picture Experts Group Layer-3 (MP3), Advanced Audio Coding (AAC), Adaptive Multi-Rate (AMR) audio codec, Joint Photographic Experts Group (JPEG or TPG), or Portable Network Graphics (PNG)), graphics libraries (e.g., an OpenGL framework used to render in two dimensions (2D) and three dimensions (3D) in a graphic content on a display), database libraries (e.g., SQLite to provide various relational database functions), web libraries (e.g., WebKit to provide web browsing functionality), and the like. The libraries 1010 can also include a wide variety of other libraries 1028 to provide many other APIs to the applications 1006.

The frameworks 1008 provide a common high-level infrastructure that is used by the applications 1006, For example, the frameworks 1008 provide various graphical user interface (GUI) functions, high-level resource management, and high-level location services. The frameworks 1008 can provide a broad spectrum of other APIs that can be used by the applications 1006, some of which may be specific to a particular operating system or platform.

In an example, the applications 1006 may include a home application 1036, a contacts application 1030, a browser application 1032, a book reader application 1034, a location application 1042, a media application 1044, a messaging application 1046, a game application 1048, and a broad assortment of other applications such as a third-party application 1040. The applications 1006 are programs that execute functions defined in the programs. Various programming languages can be employed to create one or more of the applications 1006, structured in a variety of manners, such as object-oriented programming languages (e.g., Objective-C, Java, or C++) or procedural programming languages (e.g., C or assembly language). In a specific example, the third-party application 1040 (e.g., an application developed using the ANDROID™ or IOS™ software development kit (SDK) by an entity other than the vendor of the particular platform) may be mobile software running on a mobile operating system such as IOS™, ANDROID™, WINDOWS® Phone, or another mobile operating system.

In this example, the third-party application 1040 can invoke the API calls 1050 provided by the operating system 1012 to facilitate functionality described herein.

Glossary

"Carrier signal" refers to any intangible medium that is capable of storing, encoding, or carrying instructions for execution by the machine, and includes digital or analog communications signals or other intangible media to facilitate communication of such instructions. Instructions may be transmitted or received over a network using a transmission medium via a network interface device.

"Client device" refers to any machine that interfaces to a. communications network to obtain resources from one or more server systems or other client devices. A client device may be, but is not limited to, a mobile phone, desktop computer, laptop, portable digital assistants (PDAs), smartphones, tablets, ultrabooks, netbooks, laptops, multi-processor systems, microprocessor-based or programmable consumer electronics, game consoles, set-top boxes, or any other communication device that a user may use to access a network.

"Communication network" refers to one or more portions of a network that may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other types of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (CPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organizations, other long-range protocols, or other data transfer technology.

"Component" refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components.

A "hardware component" is a tangible unit capable of performing certain operations and may be configured or arranged in a certain physical manner. In various example embodiments, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein. A hardware component may also be implemented mechanically, electronically, or any suitable combination thereof. For example, a hardware component may include dedicated circuitry or logic that is permanently configured to perform certain operations. A hardware component may be a special-purpose processor, such as a field-programmable gate array (FPGA) or an application specific integrated circuit (ASIC). A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform e configured functions and are no longer general-purpose processors.

It will be appreciated that the decision to implement a hardware component mechanically, in dedicated and permanently configured circuitry, or in temporarily configured circuitry (e.g., configured by software), may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time. Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output. Hardware components may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors 902 or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some example embodiments, the processors or processor-implemented components may be located in a single geographic location (e.g., within a home environment, an office environment, or a server farm). In other example embodiments, the processors or processor-implemented components may be distributed across a number of geographic locations.

"Computer-readable storage medium" refers to both machine-storage media and transmission media. Thus, the terms include both storage devices/media and carrier waves/modulated data signals. The terms "machine-readable medium," "computer-readable medium" and "device-readable medium" mean the same thing and may be used interchangeably in this disclosure.

"Ephemeral message" refers to a message that is accessible for a time-limited duration. An ephemeral message may be a text, an image, a video and the like. The access time for the ephemeral message may be set by the message sender. Alternatively, the access time may be a default setting or a setting specified by the recipient. Regardless of the setting technique, the message is transitory.

"Machine storage medium" refers to a single or multiple storage devices and media (e.g., a centralized or distributed database, and associated caches and servers) that store executable instructions, routines and data. The term shall accordingly be taken to include, but not be limited to, solid-state memories, and optical and magnetic media, including memory internal or external to processors. Specific examples of machine-storage media, computer-storage media and device-storage media include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks The terms "machine-storage medium," "device-storage medium," "computer-storage medium" mean the same thing and may be used interchangeably in this disclosure. The terms "machine-storage media," "computer-storage media," and "device-storage media" specifically exclude carrier waves, modulated data. signals, and other such media, at least some of which are covered under the term "signal medium."

"Non-transitory computer-readable storage medium" refers to a tangible medium that is capable of storing, encoding, or carrying the instructions for execution by a machine.

"Signal medium" refers to any intangible medium that is capable of storing, encoding, or carrying the instructions for execution by a machine and includes digital or analog communications signals or other intangible media to facilitate communication of software or data. The term "signal medium" shall be taken to include any form of a modulated data signal, carrier wave, and so forth. The term "modulated data signal" means a signal that has one or more of its characteristics set or changed in such a matter as to encode information in the signal. The terms "transmission medium" and "signal medium" mean the same thing and may be used interchangeably in this disclosure.

Changes and modifications may be made to the disclosed embodiments without departing from the scope of the present disclosure. These and other changes or modifications are intended to be included within the scope of the present disclosure, as expressed in the following claims.

What is claimed is:

1. A method comprising:
    receiving, by one or more processors, a video that includes a depiction of a body of a user;
    detecting, by the one or more processors, a plurality of skeletal joints of the body depicted in the video;
    tracking movement of the plurality of skeletal joints across a set of frames of the video; and
    smoothing the movement of a first set of the plurality of skeletal joints between frames in the first set of frames independently of smoothing movement of a second set of the plurality of skeletal joints in the first set of frames.

2. The method of claim 1, further comprising controlling an amount of smoothing that is applied the first set of the plurality of skeletal joints based on a signal stability parameter.

3. The method of claim 1, wherein the first set of the plurality of skeletal joints includes a first pair adjacent joints, and wherein the second set of the plurality of skeletal joints includes a second pair adjacent joints.

4. The method of claim 1, further comprising:
    applying a first set of smoothing filters to the first set of the plurality of skeletal joints;
    applying a second set of smoothing filters e second set of the plurality skeletal joints; and
    adapting a first parameter of the first set of smoothing filters independently of a second parameter of the second set of smoothing filters.

5. The method of claim 4, wherein the first and second sets of the smoothing filters includes a plurality smoothing filters.

6. The method of claim 4, further comprising:
    computing a first signal stability parameter that represents a first amount of noise resulting from the movement of the first set of the plurality of skeletal joints between the frames in the first set of frames; and
    modifying the first parameter based on a value of the first signal stability parameter.

7. The method of claim 6, further comprising modifying the first parameter to increase an amount of smoothing applied by the first set of smoothing filters to a second set of frames in response to determining that the first amount of noise represented by the first signal stability parameter exceeds a threshold value.

8. The method of claim 7, further comprising:
computing a second signal stability parameter that represents a second amount of noise resulting from the movement of the second set of the plurality of skeletal joints between the frames in the first set of frames; and
modifying the second parameter based on a value of the second signal stability parameter.

9. The method of claim 8, further comprising modifying the second parameter to decrease an amount of smoothing applied by the second set of smoothing filters to the second set of frames in response to determining that the second amount of noise represented by the first signal stability parameter is less than the threshold value.

10. The method of claim 4, wherein applying the first set of smoothing filters to the first set of the plurality of skeletal joints comprises applying a plurality of smoothing filters in parallel to the first set of the plurality of skeletal joints.

11. The method of claim 10, further comprising interpolating outputs of the plurality of smoothing filters.

12. The method of claim 11, wherein the interpolating of the outputs is performed based on a signal stability parameter representing an amount of noise between the outputs of the plurality of smoothing filters.

13. The method of claim 1, further comprising generating an avatar based on smoothing movement of the plurality of skeletal joints.

14. A system comprising:
a processor configured to perform operations comprising:
receiving a video that includes a depiction of a body of a user;
detecting a plurality of skeletal joints of the body depicted in the video;
tracking movement of the plurality of skeletal joints across a set of frames of the video; and
smoothing the movement of a first set of the plurality of skeletal joints between frames in the first set of frames independently of smoothing movement of a second set of the plurality of skeletal joints in the first set of frames.

15. The system of claim 14, wherein the operations further comprise controlling an amount of smoothing that is applied the first set of the plurality of skeletal joints based on a signal stability parameter.

16. The system of claim 14, wherein the first set of the plurality of skeletal joints includes a first pair adjacent joints, and wherein the second set of the plurality of skeletal joints includes a second pair adjacent joints.

17. The system of claim 14, wherein the operations further comprise:
applying a first set of smoothing filters to the first set of the plurality of skeletal joints;
applying a second set of smoothing filters e second set of the plurality skeletal joints; and
adapting a first parameter of the first set of smoothing filters independently of a second parameter of the second set of smoothing filters.

18. The system of claim 17, wherein the first and second sets of the smoothing filters includes a plurality smoothing filters.

19. The system of claim 17, wherein the operations further comprise:
computing a first signal stability parameter that represents a first amount of noise resulting from the movement of the first set of the plurality of skeletal joints between the frames in the first set of frames; and
modifying the first parameter based on a value of the first signal stability parameter.

20. A non-transitory machine-readable storage medium that includes instructions that, when executed by one or more processors of a machine, cause the machine to perform operations comprising:
receiving a video that includes a depiction of a body of a user;
detecting a plurality of skeletal joints of the body depicted in the video;
tracking movement of the plurality of skeletal joints across a set of frames of the video; and
smoothing the movement of a first set of the plurality of skeletal joints between frames in the first set of frames independently of smoothing movement of a second set of the plurality of skeletal joints in the first set of frames.

* * * * *